(12) United States Patent
Soysa et al.

(10) Patent No.: US 12,397,124 B2
(45) Date of Patent: Aug. 26, 2025

(54) BREATHING ASSISTANCE APPARATUS USER INTERFACE

(71) Applicant: FISHER & PAYKEL HEALTHCARE LIMITED, Auckland (NZ)

(72) Inventors: Warushahennedige Hansinie Soysa, Auckland (NZ); Ada Yiwen Shou, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1203 days.

(21) Appl. No.: 15/029,189

(22) PCT Filed: Oct. 21, 2014

(86) PCT No.: PCT/NZ2014/000220
§ 371 (c)(1),
(2) Date: Apr. 13, 2016

(87) PCT Pub. No.: WO2015/060729
PCT Pub. Date: Apr. 30, 2015

(65) Prior Publication Data
US 2016/0256642 A1 Sep. 8, 2016

Related U.S. Application Data

(60) Provisional application No. 62/032,387, filed on Aug. 1, 2014, provisional application No. 61/893,758, filed on Oct. 21, 2013.

(51) Int. Cl.
*A61M 16/00* (2006.01)
*A61M 13/00* (2006.01)
(Continued)

(52) U.S. Cl.
CPC .... *A61M 16/0051* (2013.01); *A61M 16/0066* (2013.01); *A61M 16/024* (2017.08);
(Continued)

(58) Field of Classification Search
CPC ............ A61M 16/0051; A61M 16/024; A61M 16/0066; A61M 16/04; A61M 16/0666;
(Continued)

(56) References Cited

U.S. PATENT DOCUMENTS 4,829,998 A * 5/1989 Jackson ................ A61M 16/16
128/203.12
5,881,723 A 3/1999 Wallace et al.
(Continued)

FOREIGN PATENT DOCUMENTS

WO WO 2013/151448 10/2013
WO WO 2015/060729 10/2014

OTHER PUBLICATIONS

International Search Report; PCT/NZ2014/000220, dated Feb. 17, 2015 in 8 pages.

*Primary Examiner* — Tu A Vo
(74) *Attorney, Agent, or Firm* — Knobbe Martens Olson & Bear LLP

(57) ABSTRACT

A breathing assistance apparatus user interface is described that presents operational modes, warnings, user instructions, fault conditions, status, menu options, hidden options, screens, panels and the like.

17 Claims, 22 Drawing Sheets

(51) Int. Cl.
*A61M 16/04* (2006.01)
*A61M 16/06* (2006.01)
*A61M 16/10* (2006.01)
*A61M 16/16* (2006.01)
*G06F 3/04886* (2022.01)

(52) U.S. Cl.
CPC ........ *A61M 16/04* (2013.01); *A61M 16/0666* (2013.01); *A61M 16/1075* (2013.01); *A61M 16/16* (2013.01); *G06F 3/04886* (2013.01); *A61M 13/003* (2013.01); *A61M 2205/18* (2013.01); *A61M 2205/3368* (2013.01); *A61M 2205/505* (2013.01); *A61M 2205/584* (2013.01); *A61M 2205/59* (2013.01); *A61M 2240/00* (2013.01)

(58) Field of Classification Search
CPC .............. A61M 16/1075; A61M 16/16; A61M 13/003; A61M 2205/18; A61M 2205/3368; A61M 2205/505; A61M 2205/584; A61M 2205/59; A61M 2240/00; G06F 3/04886
See application file for complete search history.

(56) References Cited

U.S. PATENT DOCUMENTS

| | | | |
|---|---|---|---|
| 8,190,223 B2 | 5/2012 | Al-Ali et al. | |
| 8,547,209 B2 | 10/2013 | Kiani et al. | |
| 2003/0217964 A1* | 11/2003 | Eu | A61M 1/28 210/500.1 |
| 2004/0034287 A1* | 2/2004 | Hickle | A61B 5/1106 600/300 |
| 2005/0256444 A1* | 11/2005 | O'Mahony | A61M 1/3607 604/4.01 |
| 2006/0042631 A1* | 3/2006 | Martin | A61B 5/0836 128/207.18 |
| 2006/0111749 A1* | 5/2006 | Westenskow | A61M 16/00 607/5 |
| 2008/0072896 A1 | 3/2008 | Setzer et al. | |
| 2008/0200868 A1* | 8/2008 | Alberti | A61M 1/28 604/29 |
| 2008/0300572 A1* | 12/2008 | Rankers | A61B 5/14532 604/504 |
| 2009/0301482 A1 | 12/2009 | Burton et al. | |
| 2010/0024816 A1* | 2/2010 | Weinstein | A61M 16/16 128/203.27 |
| 2010/0107076 A1* | 4/2010 | Grohman | F24F 11/30 715/709 |
| 2010/0132707 A1 | 6/2010 | Muller | |
| 2010/0229867 A1* | 9/2010 | Bertinetti | A61M 16/0051 128/205.25 |
| 2011/0040247 A1* | 2/2011 | Mandro | A61M 5/14244 604/66 |
| 2011/0071465 A1* | 3/2011 | Wang | A61M 1/28 604/67 |
| 2011/0132368 A1 | 6/2011 | Sanchez et al. | |
| 2011/0132370 A1* | 6/2011 | Farrugia | A61M 16/0051 128/204.23 |
| 2011/0138323 A1 | 6/2011 | Skidmore et al. | |
| 2011/0144616 A1* | 6/2011 | Michaud | F16J 15/56 604/153 |
| 2011/0154241 A1* | 6/2011 | Skidmore | A61M 16/0051 715/771 |
| 2011/0259333 A1* | 10/2011 | Sanchez | G09G 3/3426 128/204.23 |
| 2011/0265024 A1 | 10/2011 | Leone et al. | |
| 2011/0298621 A1* | 12/2011 | Shanbhag | A61B 5/7435 340/573.1 |
| 2012/0238851 A1* | 9/2012 | Kamen | A61M 5/14244 604/151 |
| 2012/0240927 A1* | 9/2012 | Bathe | A61M 16/085 128/203.12 |
| 2013/0008438 A1* | 1/2013 | Sugawara | A61M 16/0672 128/202.24 |
| 2013/0025596 A1* | 1/2013 | Jafari | A61M 16/0051 128/204.23 |
| 2013/0125883 A1* | 5/2013 | Bonassa | A61M 16/024 128/204.23 |
| 2013/0239961 A1 | 9/2013 | Ross, Jr. et al. | |
| 2013/0324872 A1* | 12/2013 | Babaeizadeh | A61B 5/0836 600/532 |
| 2014/0123979 A1* | 5/2014 | Doyle | A61M 16/0057 128/204.23 |
| 2014/0137870 A1* | 5/2014 | Barlow | A61M 16/0605 128/205.25 |
| 2014/0251328 A1* | 9/2014 | Graboi | A61M 16/0875 128/202.27 |
| 2014/0282181 A1* | 9/2014 | Declerck | A61M 1/38 715/771 |
| 2015/0133809 A1* | 5/2015 | Paul | A61M 16/0003 128/205.25 |

\* cited by examiner

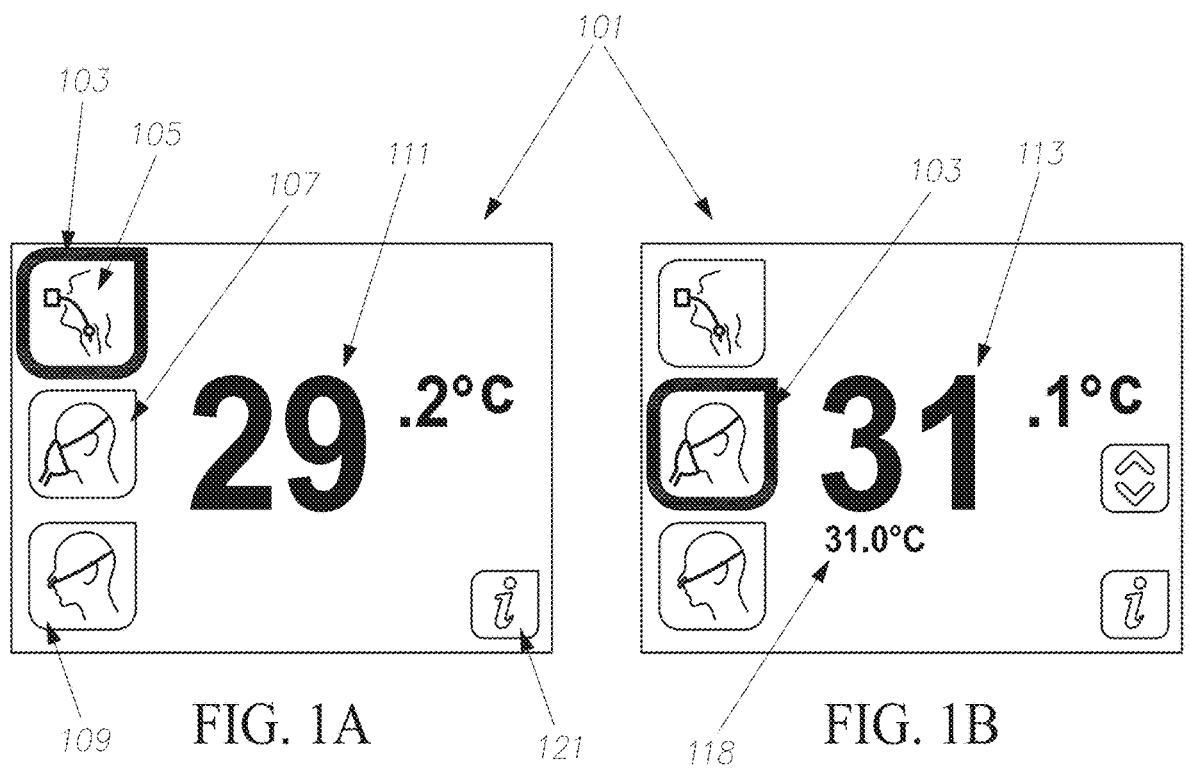

BREATHING ASSISTANCE APPARATUS USER INTERFACE

CROSS-REFERENCE TO RELATED APPLICATIONS

This application claims priority to U.S. Provisional Application No. 61/893,758, entitled "BREATHING ASSISTANCE APPARATUS USER INTERFACE," filed Oct. 21, 2013, and to U.S. Provisional Patent Application No. 62/032,387, entitled "BREATHING ASSISTANCE APPARATUS USER INTERFACE," filed Aug. 1, 2014. Each of the foregoing applications is incorporated by reference herein in its entirety.

BACKGROUND

Field

The present disclosure relates generally to a user interface for a breathing assistance apparatus and more particularly to graphical user interface features that convey information about and provide control of a breathing assistance apparatus.

Description of Related Art

A variety of devices can be used to assist with the breathing of a patient. Some of these devices are used among a plurality of users and are used almost continuously. Some of the devices are used by very few users and are used intermittently. These devices can deliver a heated and/or humidified flow of breathing gases to the user.

Although these devices are generally operated by trained health professionals, configuration and management of these devices can be difficult and time consuming. The devices may have multiple modes of operation and multiple operating conditions or events that require action of a user. In some instances, such conditions may be indicated by a numerical fault code, requiring the user to consult a look-up table or call a technician. In some instances, it may be difficult to quickly assess the operating modes and conditions of the devices to efficiently manage the devices.

SUMMARY

Accordingly, a breathing assistance or respiratory support apparatus is described that includes a display for illustrating or presenting information related to the management of the apparatus.

In a first aspect, a breathing assistance apparatus is provided that includes a display configured to provide visual information to a user. The display can present different modes of operation, such as, for example, operating modes corresponding to different types of respiratory support that can be provided using the apparatus. The display can also present different types of operational parameters, such as, for example, gases properties measured by sensors of the breathing assistance apparatus that are related or relevant to the type of respiratory support provided. In an embodiment, each operating mode is associated with a unique color or visual scheme. All other buttons, associated screens, panels, and options that are associated with each mode of operation are displayed according to the corresponding color or visual scheme of that mode of operation. In an embodiment, the display comprises a touchscreen configured to provide a way for the user to interact with the breathing assistance apparatus. For example, the display can provide elements on the touchscreen (e.g., buttons, toggles, images, etc.) wherein the elements are configured to allow the user to interact with the breathing assistance apparatus when touched by the user.

In an embodiment, setup and use instructions for a breathing assistance apparatus are provided through an information screen on the apparatus itself. This obviates the need for a user to store, maintain, or find paper instructions.

In an embodiment, when an alarm condition is present, an alarm assistance screen can be presented to direct a user how to resolve the issue. If multiple alarms are detected, the most severe alarm is displayed. If multiple potential solutions are possible for a given alarm, the breathing assistance apparatus repeatedly cycles through each possible solution. When an alarm is resolved, the display can be returned to the screen presented before the alarm condition was triggered.

In an embodiment, when a peripheral component, such as a breathing circuit, is connected to a breathing assistance apparatus, an identity associated with the component can be automatically detected. For example, in one embodiment, a coded resistor or other identifying electronic circuitry is used to indicate the type of component attached. A breathing circuit as used herein can include a tube, hose, conduit or other peripheral device. Depending on the type of component detected, for example an adult or neonatal breathing circuit, the apparatus can automatically configure itself to the appropriate operating mode and default settings.

In an embodiment, available respiratory support settings can be automatically customized according to the operating mode selected. For example, an operating mode corresponding to invasive respiratory support, or invasive operating mode, of a breathing assistance apparatus might not provide temperature set point adjustment controls by default so as to prevent undesirable temperature changes; on the other hand, in a non-invasive or mask operating mode, temperature set point, adjustment controls are provided by default. In an embodiment, these controls can be limited to a predetermined range or number of set points. In an embodiment, advanced options settings can be provided to allow a user to configure whether to allow or disable temperature set point adjustments or other control options. In an embodiment, temperature set point adjustment controls might be provided in an invasive operating mode and not in a mask operating mode, or in any or all operating modes supported by an apparatus. In an embodiment, advanced options settings can be provided to allow a user to configure default settings, including default temperature set points for one, some, or all of the different operating modes. In some embodiments, a temperature set point can be referenced to a dewpoint or a temperature.

In an embodiment, certain breathing assistance apparatus adjustment settings can be hidden to prevent casual users from adjusting settings inadvertently or undesirably. For example, in one embodiment, certain settings are hidden on an information screen and are accessible only after performing a touch sequence that is not obvious to a casual user. For example, an access panel can be presented that includes a logo or graphic and the touch sequence can involve touching certain aspects of the logo or graphic in a predetermined order.

In an embodiment, undesirable changes to the operating mode of the breathing assistance apparatus due to inadvertent activation of touch screen controls are prevented by requiring deliberate actions. For example, in an embodiment, an extended touch is required to shut down the apparatus. In another embodiment, the user is required to press and hold a physical shutdown button for a predetermined period of time. For example, in an embodiment, a sequence of button touches is required to change a temperature set point value. In an embodiment, distinctive confirmation buttons are presented to indicate that a user is taking a deliberate action. In an embodiment, the user is required to touch a button multiple times within a predetermined period of time to activate a certain function.

In some embodiments, the breathing assistance apparatus can be configured to retain customized set points when switching between operating modes. For example, when a temperature set point of a non-invasive operating mode is set and the user switches to an invasive operating mode and back again to the non-invasive operating mode, the customized temperature set point of the non-invasive operating mode will be used instead of a default temperature set point. In some embodiments, the breathing assistance apparatus can be configured to retain customized set points after a restart or power cycle.

In some embodiments, the breathing assistance apparatus can be configured to have a default operating mode on startup. For example, the breathing assistance apparatus can be configured to enter a non-invasive operating mode upon startup and load the relevant parameters and settings for that mode. In certain implementations, the breathing assistance apparatus can be configured to operate in whichever operating mode was used last prior to shutting down the apparatus.

In some embodiments, a user interface of the breathing assistance apparatus can include a status indicator configured to provide different images, icons, colors, animations, and/or words to convey to a user a current status of the apparatus. The status indicator can be configured to change when an operating condition of the apparatus changes. The status indicator can include images, icons, colors, animations, words, and the like that can quickly relate status information to the user. The status indicator can also be configured to draw a user's attention to the status indicator by, for example, flashing, changing color, scrolling a message, executing an animation sequence, or the like. The breathing assistance apparatus can also be configured to draw a user's attention to the status indicator by generating an audible tone or tones.

In some embodiments, the breathing assistance apparatus displays an estimated dewpoint on a display instead of or in addition to a measured gases temperature. The estimated dewpoint displayed can indicate an estimate of the dewpoint of gases being provided and/or that is being targeted by the breathing assistance apparatus. It is to be understood that, although the dewpoint may be expressed as a temperature, the dewpoint is correlated with the humidity of gases and can be different from the gases temperature. The breathing assistance apparatus can be configured to measure parameters of gases (e.g., the temperature, flow rate, etc.) at one or more locations within the apparatus in the gases flow path to estimate the dewpoint. In some embodiments, the breathing assistance apparatus may display a dewpoint set point on a display instead of or in addition to a temperature (e.g., gases temperature) set point. In some embodiments, the breathing assistance apparatus may provide a dewpoint set point adjustment control instead of or in addition to a temperature (e.g., gases temperature) set point adjustment control. In some embodiments, the breathing assistance apparatus may display a dewpoint calculation or measurement on a display instead of or in addition to a temperature calculation or measurement.

In some embodiments, the breathing assistance apparatus can be configured to display different levels of details for alarms based at least in part on a user configuration, alarm conditions, operating mode, and the like for the apparatus. The level of detail can include, for example and without limitation, likely or potential causes for the alarm, likely or potential solutions for the alarm, one or more error codes, severity and/or priority of the alarm, and the like.

BRIEF DESCRIPTION OF THE DRAWINGS

These and other features, aspects, and advantages will now be described with reference to the drawings of some embodiments, which embodiments are intended to illustrate and not to limit the scope of the disclosure.

FIG. 1A is a screenshot of a first embodiment of an invasive operating mode.

FIG. 1B is a screenshot of a first embodiment of a non-invasive operating mode.

DETAILED DESCRIPTION

Aspects of the disclosure will now be set forth in detail with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit the scope of the disclosure herein, which is instead defined by the claims following this description.

A breathing assistance apparatus can include a number of elements that function to provide gases to a user. The apparatus can be equipped with a heating and/or a humidification element and a blower.

To assist a user in operating the breathing assistance apparatus, the breathing assistance apparatus can include a display that provides information to the user in the form of text, images, animations, colors, icons, and the like. The display can be configured to display static images, semi-static images (e.g., sensor readouts), and animated images on the screen simultaneously or at the same time. Animated images can refer to video and/or to a sequence of still images. The display can be configured to update the displayed information in real time and in response to changing operating conditions, fault conditions, user selections (e.g., through a function of the user interface), events, components being connected to the breathing assistance apparatus, and the like.

In some embodiments, the breathing assistance apparatus monitors one or more characteristics of operation and, upon a triggering event occurring, the apparatus displays a series of frames such as, for example, text, real time readings, graphics, recorded images, visual descriptions, visual directions, still images, and/or videos on the display. A triggering event may comprise a single event, multiple events, or a sequence of events. The series of frames can depict one or more still graphics and/or animated actions such that the user can make an adjustment to the apparatus based upon the series of frames to address the occurrence of the triggering event.

Figure 1:
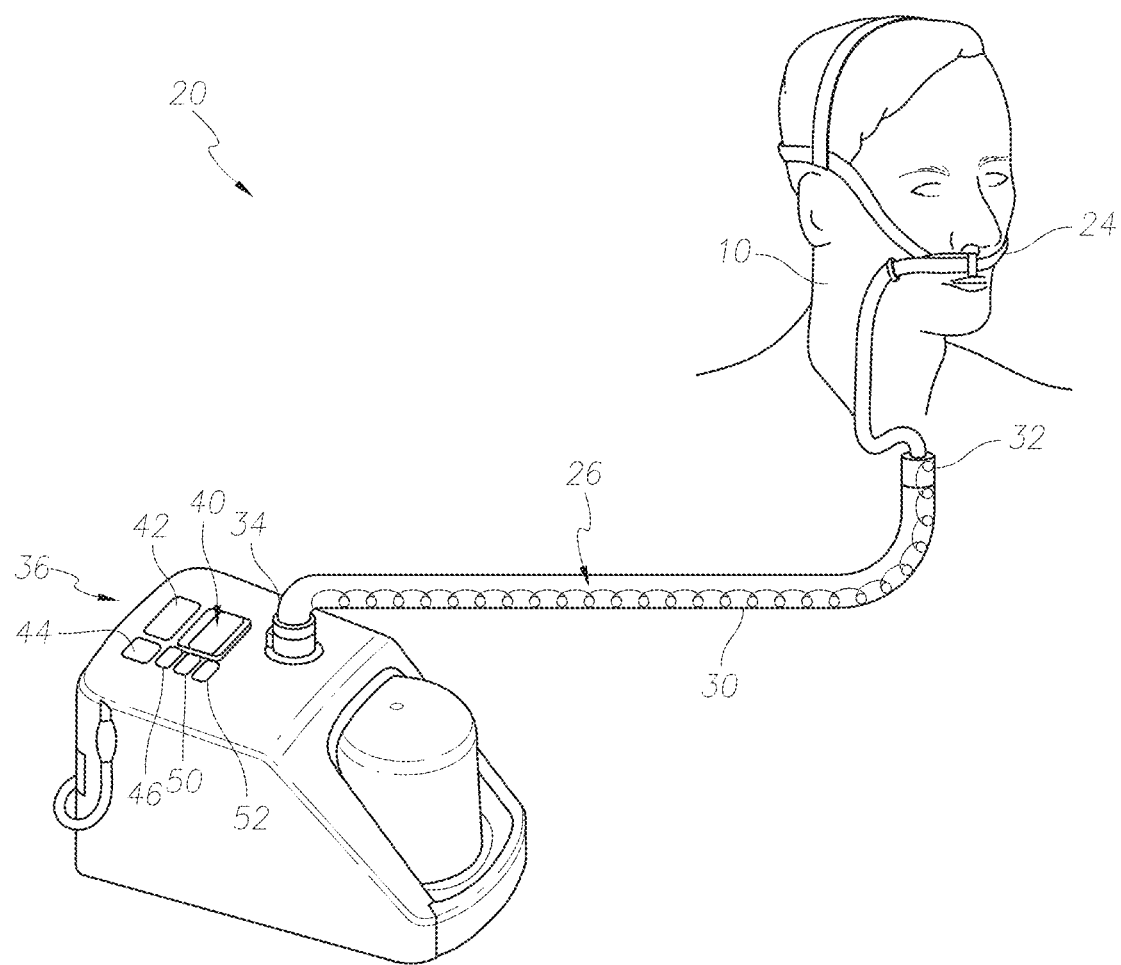
FIG. 1 is a diagram of a patient using a breathing assistance apparatus.

FIG. 1 is a diagram of an example breathing assistance apparatus 20 that provides a humidified and heated flow of fluid (e.g., gases or air) to a patient 10. The present disclosure is not intended to be limited to the illustrated breathing assistance apparatus 20, but is intended to include any breathing assistance apparatus or respiratory support apparatus. The breathing assistance apparatus 20 comprises a high-flow breathing assistance apparatus; however, features, aspects, and advantages of some embodiments can be used with other types of apparatus used to supply a flow of fluid to the patient 10. For example, features, aspects, and advantages of some embodiments can be used with CPAP machines, insufflation humidifiers for laparoscopic or other surgical procedures, respiratory humidifiers, humidifiers for non-invasive ventilation applications, humidifiers for invasive ventilation applications, neonatal resuscitation devices, and the like. Embodiments described herein can be used with the breathing assistance apparatus and display described in PCT Application No. PCT/NZ2013/000060 filed Apr. 5, 2013, which is incorporated by reference in its entirety so as to form a part of this specification.

In some embodiments, the breathing assistance apparatus 20 can include a display 40 configured to display a series of images in succession that illustrate a suggested action to the user. The series of images can be used to instruct a user on how to perform a particular action, to provide information regarding the breathing assistance apparatus 20 to the user, or to provide an indication of an operating mode of the breathing assistance apparatus 20 to the user. The series of images can be displayed in response to a triggering event and can be configured to present one or more methods of responding to the triggering event. The breathing assistance apparatus 20 can be configured to detect various triggering events and to automatically display a corresponding series of images. For example, the breathing assistance apparatus 20 can be configured to detect a fault condition. In response, the breathing assistance apparatus 20 can display a series of images to provide instructions to the user on how to correct the fault condition. In some embodiments, the series of images displayed on the display 40 can include flashing icons, coloring, shading, and/or other similar visual cues as further described with respect to FIGS. 2A-2B.

With continued reference to FIG. 1, the breathing assistance apparatus 20 can be connected to a patient interface 24 with a flexible conduit 26. As illustrated, the breathing assistance apparatus 20 includes a flow generator; however, the breathing assistance apparatus 20 can be used without an internal or built-in flow generator, such as by using a flow source external to the apparatus 20. The patient interface 24 can be any suitable patient interface. For example, but without limitation, the patient interface 24 can comprise a non-invasive interface including, but not limited to, an adult nasal cannula, neonatal nasal cannula, full face mask, combination oral/nasal mask, nasal mask, nasal pillow, high flow cannula, or the like. In some configurations, the patient interface 24 can comprise an invasive or minimally invasive interface including, but not limited to, an endotracheal tube, insufflation device, or the like. In some configurations, the patient interface 24 can comprise an adaptor or connector for coupling to a tracheotomy device or a mask.

In the illustrated configuration, the flexible conduit 26 can comprise a heating element 30, a sensing element 32, and/or a coded information element, such as a resistor (not shown). In some configurations, the sensing element 32 can be positioned at an end portion of the flexible conduit 26 closest to the patient interface 24. In some configurations, the sensing element 32 can be positioned within the lumen defined by the flexible conduit 26 such that the sensing element 32 is exposed to the fluid being carried within the lumen. The sensing element 32 can sense a characteristic or attribute of the fluid being carried within the lumen. In some configurations, the sensing element 32 can be arranged and configured to sense the temperature of the fluid passing through the lumen.

The end of the flexible conduit 26 closest to the breathing assistance apparatus 20 comprises a connector 34. In some configurations, the connector 34 can be configured to establish both a pneumatic connection between the breathing assistance apparatus 20 and, the lumen of the flexible conduit 26 and an electrical connection between any two or more of the heating element 30 of the flexible conduit 26, the coded information element, and the breathing assistance apparatus 20. In some configurations, the connector 34 facilitates establishing both the pneumatic connection and the electrical connection in a single step.

With continued reference to FIG. 1, the breathing assistance apparatus 20 comprises a user interface 36. The user interface 36 enables interaction between the user, the patient 10, or another person (e.g., without limitation, health professionals, distributors, or the like) and the breathing assistance apparatus 20. The illustrated user interface 36 comprises the display 40. The display 40 can be embodied as any suitable type of display screen or other display device. In, some configurations, the display 40 comprises an organic light-emitting diode (OLED) screen. In some configurations, the display 40 can comprise a full color display with a pixel count of between about 6,000 pixels and about 500,000 pixels. In some configurations, the display 40 can comprise a pixel count of about 20,480 pixels. In some configurations, the display 40 can comprise a screen size of about 128 pixels by about 160 pixels (vertical by horizontal). In some configurations, the display 40 can measure about 1.8 inches diagonally to about 4 inches diagonally. To reduce heat transferred from the display 40 to other components of the breathing assistance apparatus 20, the display 40 can be operated with a black screen (e.g., most of the pixels are inactive during operation of the breathing assistance apparatus 20).

The user interface 36 comprises a power key/button 42, a mute key/button 44, an up arrow key/button 46, a down arrow key/button 50, and a mode key/button 52. In some configurations, the user interface 36 can include some combination of mechanical keys, electro-mechanical keys, and touch-sensitive capabilities, such as where the display 40 comprises a touchscreen and navigation through a menu structure or other suitable manner of device operation can be provided via the display 40. In some configurations, a joystick, a toggle, or the like can be provided for navigation through a menu structure or other suitable manner of device operation.

The breathing assistance apparatus 20 also comprises a suitable controller, which may include memory and other components used for sensing various characteristics of flows and operation of the breathing assistance apparatus 20. Moreover, the breathing assistance apparatus 20 can comprise a speaker or other audible alert generator.

Embodiments of the display 40 are configured to provide a user with a quick and easy interface to operate the breathing assistance apparatus 20 and to be aware of the configurations and alarms of the breathing assistance apparatus 20. For example, in an embodiment, each different operating mode is presented using a different or distinctive color or visual scheme. As explained in greater detail below, these colors or schemes are also used in the settings options such that all buttons and banners change colors to reflect to the user that the breathing assistance apparatus 20 is in a particular mode of operation. In an embodiment, different or distinctive color or visual schemes are used to present different patient types, changes in measured temperature, and/or other changes in operational state.

Figure 1C:
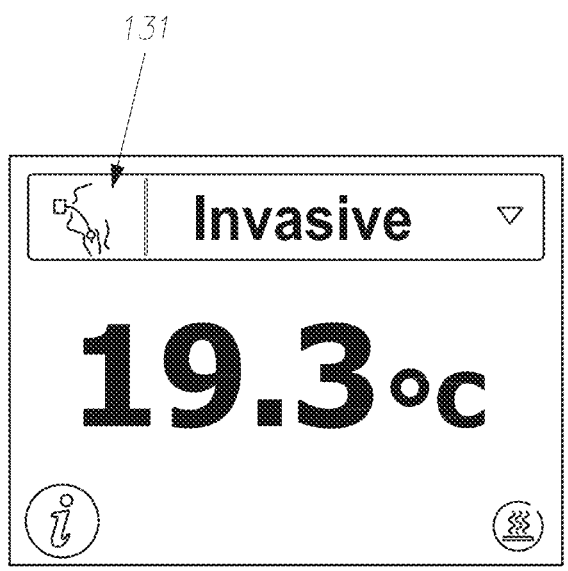
FIG. 1C is a screenshot of a second embodiment of an invasive operating mode.
Figure 1D:
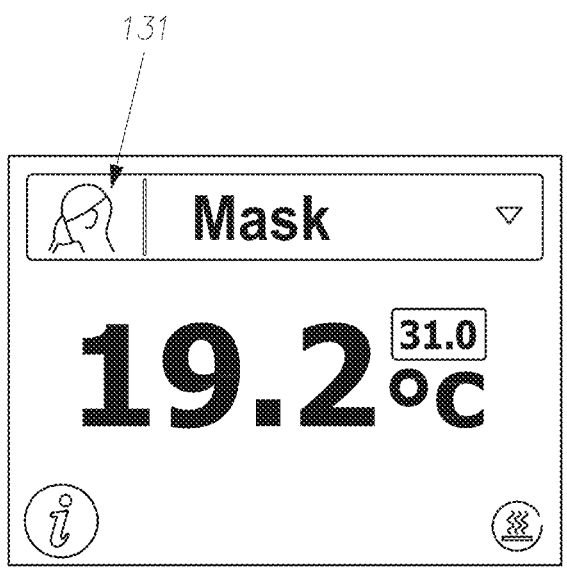
FIG. 1D is a screenshot of a second embodiment of a non-invasive operating mode.

FIGS. 1A-1D are screenshots that illustrate different operating modes of the breathing assistance apparatus 20. In these embodiments, each operating mode corresponds to a different type of respiratory support provided by the breathing assistance apparatus 20. For example, FIGS. 1A and 1C illustrate two embodiments of an invasive operating mode. FIGS. 1B and 1D illustrate two embodiments of a non-invasive operating mode.

In FIGS. 1A and 1B, an invasive operating mode indicator 105, a non-invasive operating mode indicator 107, and an Optiflow™ operating mode indicator 109 are all displayed at the same time on the screen in a vertical column on right. Optiflow™ operating mode is an operating mode corresponding to nasal high flow respiratory support. Alternatively, the various indicators can be displayed in a horizontal row across the top, middle, or bottom of the screen or in a vertical column along the left or middle of the screen. As explained in greater detail below with respect to FIGS. 5A-5E, each different mode of operation receives a unique color or visual scheme. For example, the invasive operating mode indicator 105 is displayed using a dark blue color, the non-invasive operating mode indicator 107 is displayed using a medium blue color, and the Optiflow™ operating mode indicator 109 is displayed using light blue color.

In some embodiments, the breathing assistance apparatus 20 can be configured to operate in a customizable default operating mode on startup. For example, using an advanced menu or other method, a user can configure the breathing assistance apparatus 20 to operate in, an invasive operating mode upon startup. The breathing assistance apparatus 20 would then load the settings relevant to the selected default operating mode after any initialization procedures performed on startup. This can be advantageous in an environment (such as, for example, a surgical ward) where the breathing assistance apparatus 20 will generally or likely operate in a particular operating mode (e.g., an invasive operating mode). The default operating mode can be, for example, an invasive operating mode, a non-invasive operating mode, or an Optiflow™ operating mode. The breathing assistance apparatus 20 can be configured to allow the user to change the default startup operating mode at any time.

In some embodiments, the breathing assistance apparatus 20 can be configured to remember the most recently used operating mode when it is shut down and then return to the remembered operating mode after startup.

As shown in FIGS. 1A and 1B, a selected operating mode of the plurality of operating modes can be highlighted to indicate to the user which of the plurality of operating modes is currently operating on the breathing assistance apparatus 20. In FIG. 1A, the invasive operating mode selection button 105 is outlined or highlighted in a green color 103 to indicate that it is the selected and current operating mode. In FIG. 1B, the non-invasive operating mode indicator 107 is outlined or highlighted to indicate it is operating on the breathing assistance apparatus 20. This highlighting provides a user the ability to quickly identify the current mode of operation.

In an embodiment, when selecting a different operating mode, the highlighted border that indicates the currently selected operating mode is shifted from the operating mode that was selected to the newly selected operating mode. A confirmation panel will then be displayed. The panel will request the user to confirm or cancel the request to change the operating mode in text format. The text will specify the operating mode to which the breathing assistance apparatus 20 will switch upon receiving confirmation. Specifying the new operating mode is also a risk control in case the caregiver does not understand the symbol on the operating mode button that they have touched. This panel contains a 'confirm' button and a 'cancel' button. If the caregiver clicks the cancel button, the panel is hidden and the highlighted border will shift back to the operating mode button that was previously selected. On clicking the confirm button, the panel will be hidden and the highlighted border will remain around the newly selected operating mode. The confirm and cancel buttons can include a distinctive color or shape to distinguish them from other user interface buttons.

In FIGS. 1C and 1D, the user can touch an operating mode bar 131 to reveal the other operating modes available. An arrow pointing down on the right side of the button can be used to indicate to the user that more operating modes are available. Upon touching the bar, the two remaining operating. modes can drop down below the bar. The arrow on the right side can turn to point to the left to indicate the currently selected operating mode. The user can select one of these two remaining operating modes to change the operating mode. In an embodiment, after a predetermined period of time, if the user does not select a different operating mode, the two remaining operating modes that had dropped down can collapse back into the operating mode bar 131 and the operating mode currently running can be shown.

Returning to FIGS. 1A and 1B, depending on the operating mode selected, the default parameters are automatically configured. For example, in a non-invasive operating mode, a temperature set point 118 is automatically set to 31.0° C. (degrees Celsius), or the default set point elected for this operating mode. The temperature set point 118 may refer to the desired operating gases temperature or the desired operating dewpoint. Temperatures 111 and 113 indicate the measured gases temperatures or the estimated dewpoints. An invasive operating mode screen illustrated in FIG. 1A does not display the desired or default set point because the set point is set to a default value and is not changeable in this embodiment. In other embodiments, the temperature set point may be adjustable in an invasive operating mode.

Temperatures 111 and 113 can be configured to display numbers that correspond to estimated dewpoints of the delivered gases rather than measured gases temperatures. This can advantageously help a user to understand operation of the breathing assistance apparatus 20 and/or deliver more efficacious respiratory support because the breathing assistance apparatus 20 can be configured to provide gases at a targeted or desired humidity having a suitable temperature. Displaying the estimated dewpoint can reduce confusion for a user (e.g., a clinician), as the targeted or desired characteristic of the gases is the humidity of the gases at a suitable temperature, both of which can be understood from the estimated dewpoint of the gases. The temperature of the gases may not be sufficient information for the user as an estimate of the humidity and temperature of the gases may be of greater therapeutic importance than the temperature alone.

The breathing assistance apparatus 20 can be configured to provide gases with a targeted dewpoint by controlling the amount of power delivered to a heater plate and/or other heaters in the gases flow path. The estimated dewpoints displayed by temperatures 111 and 113 can indicate estimates of the dewpoints of gases being provided and/or that is being targeted by the breathing assistance apparatus 20. The breathing assistance apparatus 20 can be configured to measure parameters of the gases (e.g., the temperature, flow rate, etc.) at one or more locations in the gases flow path to estimate the dewpoint. In some embodiments, the correlation between the measured parameters and the estimated dewpoint is provided by an algorithm, equation, look-up table, or the Like. Parameters used to correlate measured temperature(s) and the estimated dewpoint can be based at least in part on empirical studies of the breathing assistance apparatus 20.

In an embodiment, the display 40 can include a status indicator that shows an icon and/or words to indicate a status of the breathing assistance apparatus 20 to provide an easy and quick way to assess the operating condition of the breathing assistance apparatus 20. The breathing assistance apparatus 20 can be configured, for example, to assess an internal status of the breathing assistance apparatus 20 and display a suitable indicator, such as a green tick mark, if things are running within acceptable parameters. The status indicator can also be configured to signal or suggest to a user to perform certain actions such as, for example and without limitation, shut down, reset, connect patient, and the like. The status indicator can also be configured to provide information to a user to allow the user to make informed decisions with respect to operating the breathing assistance apparatus 20. For example, the status indicator can indicate to a user that temperature overshoots may be expected, the breathing assistance apparatus 20 is heating, the breathing assistance apparatus 20 is in a transition stage, the breathing assistance apparatus 20 is in a standby mode and/or is not in a normal mode of operation, or the like. The status indicator can include icons, colors, words, and the like that can quickly relate status information to the user. The status indicator can also be configured to draw the user's attention to the indicator by, for example, flashing, changing color, scrolling a message, or the like. In some embodiments, the breathing assistance apparatus 20 can be configured to generate an audible signal configured to provide similar and/or complementary status information and/or to draw a user's attention to the breathing assistance apparatus 20.

In some embodiments, the breathing assistance apparatus 20 can enter a holding mode. The holding mode can be entered, for example and without limitation, when operating conditions are outside expected or configured ranges. The holding mode can cease (e.g., return to a selected operating mode, such as the operating mode being used when the holding mode initiated) when normal, expected, or selected operating conditions resume. In some embodiments, the holding mode may be entered manually and can be configured to allow a user to exit the holding mode at the user's convenience such as when it is no longer effective or safe for the user to be operating in the holding mode. In some embodiments, during the holding mode, the user interface of the breathing assistance apparatus 20 can include a status indicator configured to provide different images, icons, animations colors, and/or words to convey to a user that the breathing assistance apparatus is in the holding mode. The status indicator can also be configured to draw a user's attention to the indicator by, for example, flashing, changing color, scrolling a message, generating a periodic or continuous melody or single note, or the like.

Figure 2A:
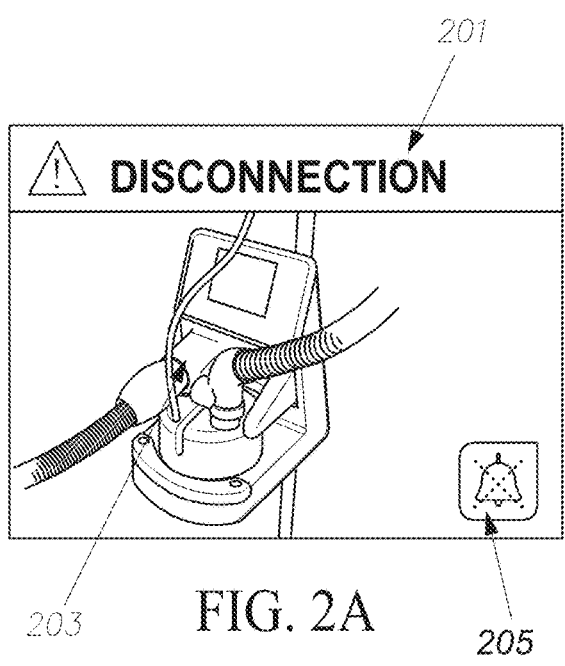
FIG. 2A is a screenshot of an alarm highlighting a component of a breathing assistance apparatus that requires attention
Figure 2B:
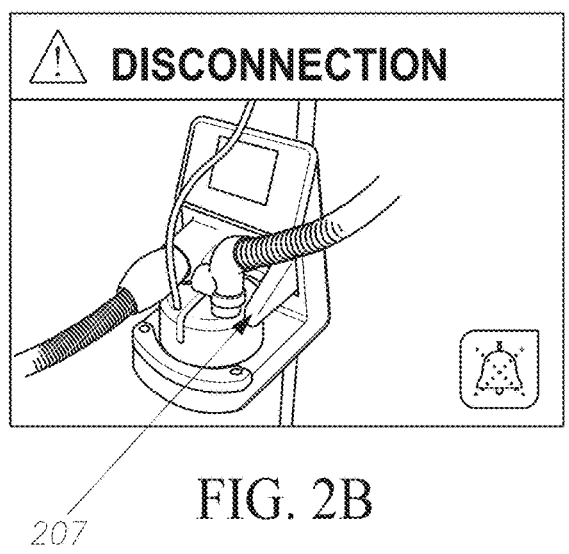
FIG. 2B is a screenshot of an alarm displaying a close-up of a component of a breathing assistance apparatus.

FIGS. 2A and 2B illustrate embodiments of user interface alarm screens. When an alarm condition is detected, an alarm screen will be brought up automatically with an audible alarm component to notify the user. A dedicated alarm screen is used such that the user's focus can be drawn to the issue at hand and not distracted by information that is not necessary for resolving the issue. If multiple alarm conditions are present, the alarm screen for the most severe alarm condition detected is displayed. In some embodiments, when a given alarm is resolved, the next most severe alarm will next be displayed. In certain embodiments, other prioritizations of multiple alarms may be used. For example, multiple alarms may be prioritized by the order in which they occurred, by predetermined modal importance (e.g., an alarm may be less important during start-up of the breathing assistance apparatus than during later operation), or by any combination of these or the like.

The corrective action to be taken by the caregiver will be presented under the title banner in text format or text and image or animation format or purely using an animation. This information is displayed on the display 40 to ensure ease of use. This obviates the necessity for the primary caregiver to refer to any other external material to solve the issue encountered by the breathing assistance apparatus 20.

As shown in FIG. 2A, the alarm screen includes a description of the alarm 201, an possible solution 203 to resolve the alarm condition, and a user control to pause and/or resume the audible alarm. This can be, for example, a mute button 205. In an embodiment, the possible solution 203 can be presented using animation and/or by highlighting certain portions in an image of the breathing assistance apparatus 20. The highlighting, for example, highlights in a distinctive color the component involved in the alarm. In some embodiments, the possible solution 203 can be presented using text, with or without real time data displayed when appropriate. For example, the possible solution 203 can display text including the real time measurements of the patient end temperature for a high temperature alarm 201. In some embodiments, the possible solution 203 can contain both text and graphical elements. Once the alarm condition is resolved, the user interface will automatically switch back to the screen displayed before the alarm was triggered. In an embodiment, a paused audible alarm will, also automatically resume after a predetermined amount of time, for example, 2 minutes.

If an animation is to be shown on the alarm screen, in an embodiment, it will first show a view of the breathing assistance apparatus 20. The animation will then zoom or pan to the affected area that flashes in a distinctive color and display the corrective action. The animation will keep cycling until the issue is resolved. In an embodiment, a number of defined frames at the end of each cycle will be used to specify that the animation has ended and that it will be shown again. In an embodiment, if there is more than one possible reason for the alarm condition, all animations are shown first before they are repeated. A number of defined frames will be shown at the end of each animated solution to indicate that the issue could be one of a number of solutions. The display order of possible solutions is determined dynamically by the relevance of each possible solution to the alarm condition.

Figure 3A:
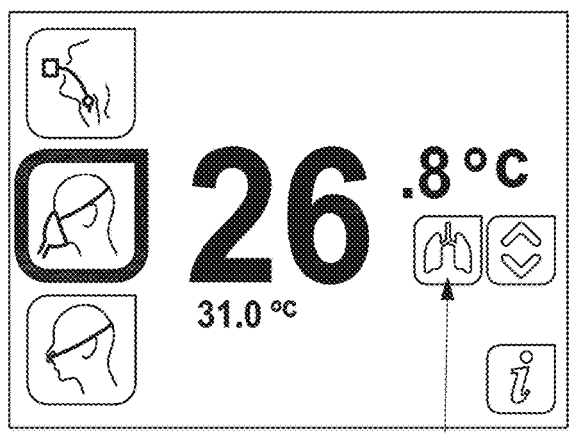
FIG. 3A is a screenshot of a warning in a first embodiment of a non-invasive operating mode.
Figure 3B:
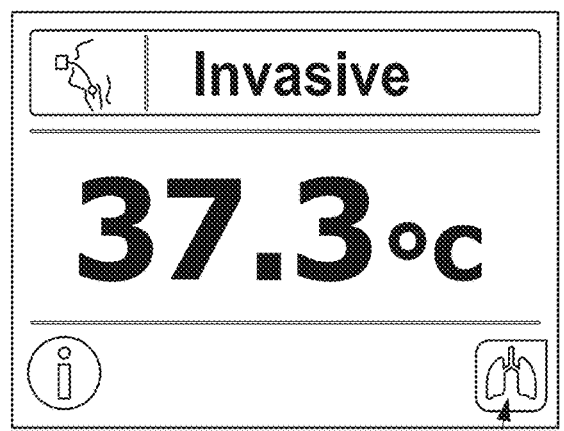
FIG. 3B is a screenshot of a warning in a second embodiment of an invasive operating mode.

In an embodiment, warning indicators can be provided as an early indication before an alarm status is reached. For example, in FIGS. 3A and 3B, indicators 303, 304 are provided. Each of the indicators 303, 304, as illustrated in one embodiment, is a yellow button with a lung symbol illustrated thereon. The indicators 303, 304 in the embodiments of FIGS. 3A and 3B indicate a low humidity state, for example. The user can then click on one of the indicators 303, 304 and the display 40 will change to a warning screen that is similar in layout to an alarm screen. An audible alarm will not sound. There will be a back button presented on this warning screen to allow the user to navigate back to the main screen. The warning screen is displayed upon touching one of the indicator buttons 303, 304 to provide information on how to resolve the warning condition such that if desired the user is able to apply the corrective action to prevent the warning state from progressing to an alarm state.

In an embodiment, indicators 303, 304 can indicate a change in operational status. For example, one or more of the consumable or peripheral devices associated with the breathing assistance apparatus 20 may be designed to have a limited life span, and the breathing assistance apparatus 20 may be configured to be able to detect whether such a consumable or peripheral device has exceeded its designated life span. When this occurs, the indicators 303, 304 may be displayed to inform the user of the change in operational status. In some embodiments, instead of or in addition to the indicators 303, 304, an informative message can be displayed through the use of a pop-up screen or window on the display 40, a separate screen on the display 40, a message box, or a graphical icon that leads to a second screen with additional details. The user can then click on one of the indicators 303, 304 and the display will change to an information screen that is similar in layout to a warning or alarm screen. There can be a back button presented on this information screen to allow the user to navigate back to the main screen. In some embodiments, the warning or informational screen can reappear at periodic intervals or upon the occurrence of an event (e.g., a change in operational mode, power-up, reset, etc.) until the triggering condition (e.g., the component that has exceeded its lifetime) has been replaced or the problem is determined to be otherwise corrected. In other embodiments, an information screen may be displayed upon the change in operational status.

The information indicators, information screens, warning indicators, warning screens, alarm indicators, and/or alarm screens can be configured to provide a customizable or selectable level of detail. A user can set the desired level of detail by accessing a settings menu, as described herein. The level of detail provided can include steps to address the most likely issue causing the warning or alarm, conditions causing the warning or alarm, potential causes for the warning or alarm, or the like. The level of detail may be restricted to operations that may be performed using the settings of the breathing assistance apparatus 20, operations that may require the user to access hardware components of the breathing assistance apparatus 20, operations that may require disassembly of portions of the breathing assistance apparatus 20, or the like. In some embodiments, a warning or alarm can provide an initial level of detail and, after an action by a user or a passage of time, the level of detail provided can increase or decrease. For example, an alarm can provide an initial level of detail indicating which alarm has been triggered. The alarm indicator or screen can include a user interface element that, when activated or selected, causes the level of detail to increase to include, for example, the most likely cause of the alarm and/or steps to take to fix or address the cause of the alarm.

In some embodiments, the warning and/or alarm screens can display only one warning or alarm at a time when there are multiple warnings or alarms. The warning or alarm to be displayed can be selected based at least in part on an assessment of risk associated with the warning or alarm, an alarm priority setting, a ranking of alarms, or the like. Once a warning or alarm has been addressed, the next warning or alarm can be shown. In some instances, multiple error codes may trigger an alarm and the breathing assistance apparatus 20 can be configured to pick a single proposed solution to display to the user, where the single solution has been determined to be the most likely solution to address the error code or codes. As described herein, animations can be displayed that instruct a user on how to address a warning or alarm.

Figure 4A:
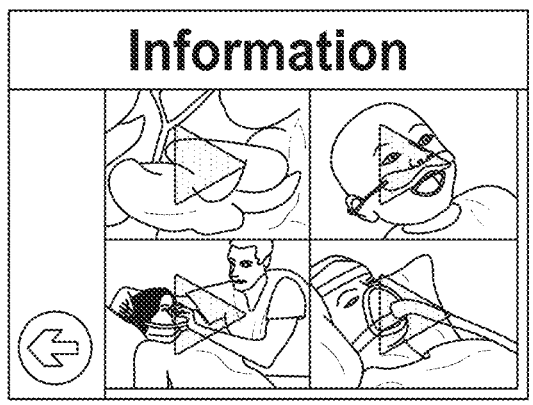
FIG. 4A is a screenshot of an information screen.
Figure 4B:
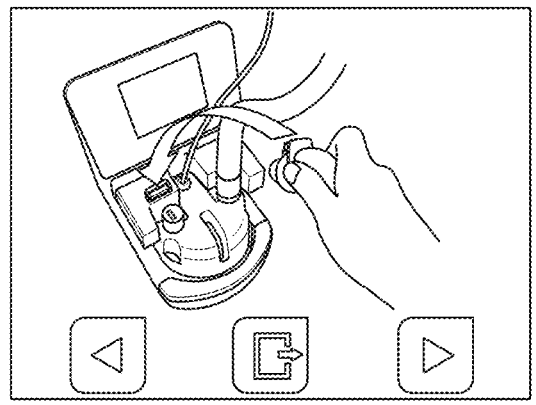
FIG. 4B is a screenshot of a tutorial instruction.

FIGS. 4A and 4B are screenshots that illustrate embodiments of a user setup and/or in-use tutorials. Hospitals have different procedures for storing medical equipment user instructions. Some hospitals store them in a separate office, some have electronic versions on a computer in an ICU or ward, and some hospitals attach laminated user instructions on the equipment. The present disclosure provides for user setup and in-use tutorial instructions to be electronically stored on the breathing assistance apparatus 20 and displayed on a display as selected by a user. These tutorials can use animated slide shows or videos to provide the user with the help to setup and operate the breathing assistance apparatus 20.

The user can press an information button 121, as illustrated in FIG. 1A, on the main screen to enter the information screen. On the information screen, the user will be given the option of accessing a setup tutorial or an in use tutorial. Each tutorial includes a series of images or video that the user can navigate through at their own pace. In an embodiment where an animation or automated slide show is presented to the user, pause, resume, fast forward and rewind options, among other control options, are provided.

In an embodiment, a controller within the breathing assistance apparatus 20 will detect when there is a type change of attached peripheral components, for example, from an adult circuit to a neonatal circuit, and change the operating mode and default settings appropriately. When an adult circuit is detected because an adult circuit is connected, a default adult operating mode is automatically selected, for example, an invasive operating mode may be automatically selected. In an embodiment, on detecting a change to a neonatal circuit, the controller will switch the operating mode to a default neonatal operating mode. In an embodiment, when a circuit is detected that corresponds to a particular type of operating mode, the breathing assistance apparatus 20 is automatically switched to that operating mode and the default settings are applied. In an embodiment, when a circuit is attached that is unidentified, a default operating mode is selected. This reduces the risks of setup error and reduces the number of set up steps required. Thus, upon detecting a circuit type change, the breathing assistance apparatus 20 provides visual feedback to the user so that at a glance the current setup can be identified without needing to look at the physical system setup, such as which circuit is attached. This is especially important when using older circuits that are unidentified, to support backwards compatibility. Moreover, this notification also acts as verification that the correct circuit is used.

The options provided for the various modes of operations include primary functionalities which are related to the operating modes and alarm conditions during operation, and supportive functionalities which are related to configuration of the breathing assistance apparatus 20, such as language selections and tutorials. All supportive functionalities are organized under information or advanced settings, for example, on an information screen. In order to emphasize the differences in functionalities, different shaped buttons are used to distinguish between primary and supportive functionalities. For example, squared buttons with slightly rounded corners are used for buttons supporting primary functionalities, whereas rounded-shaped buttons are used for supportive functionalities. In some embodiments, the breathing assistance apparatus can have a number of configurable settings including, for example and without limitation, enabling/disabling or setting control of dimming feature for the screen depending on ambient light (automatic or manual), volume control (e g, manual or automatic, on circuit change, higher volume for adult, quieter for infant), enabling/disabling expiry date reminders, software upgrade, writing parameters to configuration memory (e.g., calibration constants), set default startup mode (e.g., invasive), and/or retrieve/download logs.

Figure 5A:
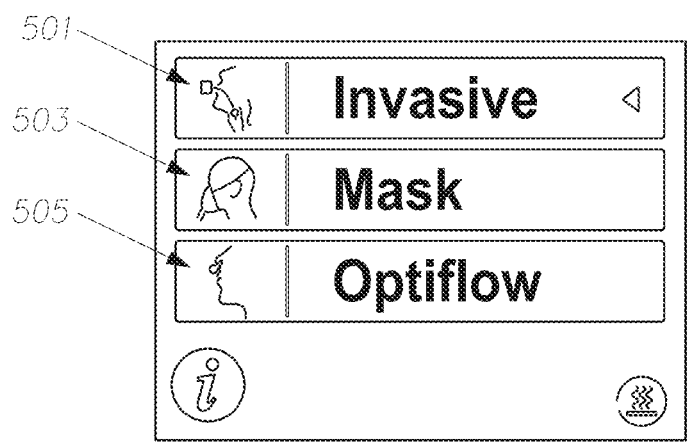
FIG. 5A is a screenshot of color coded operating modes.
Figure 5B:
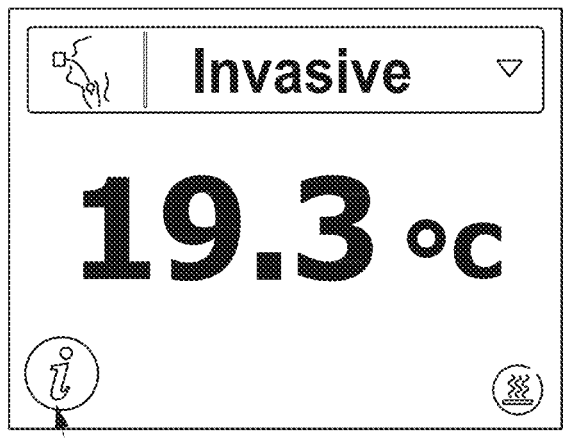
FIG. 5B is a screenshot of a color coded invasive operating mode.
Figure 5C:
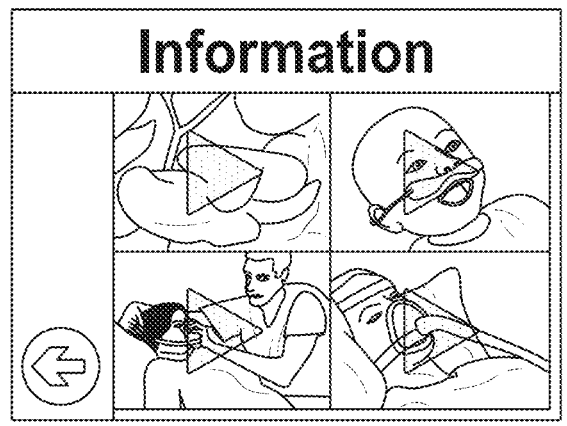
FIG. 5C is a screenshot of an information screen color coded to match an invasive operating mode.
Figure 5D:
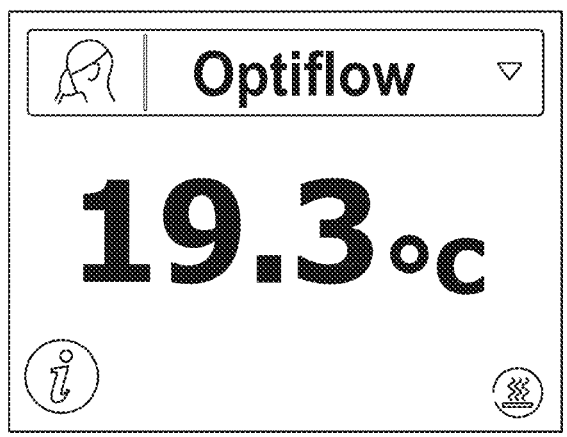
FIG. 5D is a screenshot of a color coded Optiflow™ operating mode.
Figure 5E:
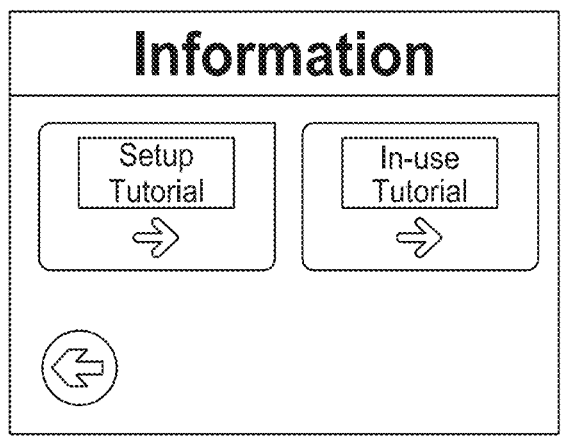
FIG. 5E is a screenshot of an information screen color coded to match an Optiflow™ operating mode.

FIG. 5A is a screenshot that illustrates another embodiment of an operating mode selection screen. This screen provides a list of operating modes from which the user can make a selection. As discussed above with respect to FIGS. 1A-1D, each operating mode is associated with a unique color or visual scheme. Thus, for example, an invasive operating mode selector 501 is associated with a dark blue color scheme, a non-invasive operating mode selector 503 is associated with a medium blue color scheme, and an Optiflow™ operating mode selector 505 is associated with a light blue color scheme. Of course, other colors or visual effects can be used to distinguish the various modes of operation. Moreover, although the embodiment illustrated in FIG. 5A provides distinction based on different shades of a single color, the disclosure is not so limited and it is to be observed that different colors, shades, shading, or other visual effects can be used. When an operating mode is selected, the visual scheme associated with that operating mode is also displayed for all screens or panels presented with respect to that operating mode. For example, FIG. 5B is a screen view of an invasive operating mode and it is shown in a dark blue, similar to that shown on the operating mode selection screen of FIG. 5A. In an embodiment, warning screens or warning panels or other screens can follow the color scheme of the selected operating mode. In some embodiments, certain screens or buttons are not provided with the same visual scheme as the selected operating mode. For example, alarm screens can have a fixed color scheme, independent of the chosen operating mode. FIG. 5C is an information screen, provided by selecting an information button 530 of FIG. 5B. The information screen of FIG. 5C is also shown in a dark blue color scheme. FIGS. 5D and 5E on the other hand illustrate an Optiflow™ operating mode screen and associated information screen respectively. As illustrated, FIGS. 5D and 5E are shown with a light blue color scheme matching that of the Optiflow™ operating mode selector 505 of FIG. 5A. Thus, a user using the information screen, will be able to quickly identify the operating mode, and thus the relevance of the instructions provided, based on the color screen displayed.

Assistive colors can also be used with 'confirm' and 'cancel' buttons on panels to provide a visual cue to users in redundancy to text. Again, embodiments can include a variety of different or clinically significant colors or other visually distinctive indicators.

Figure 6A:
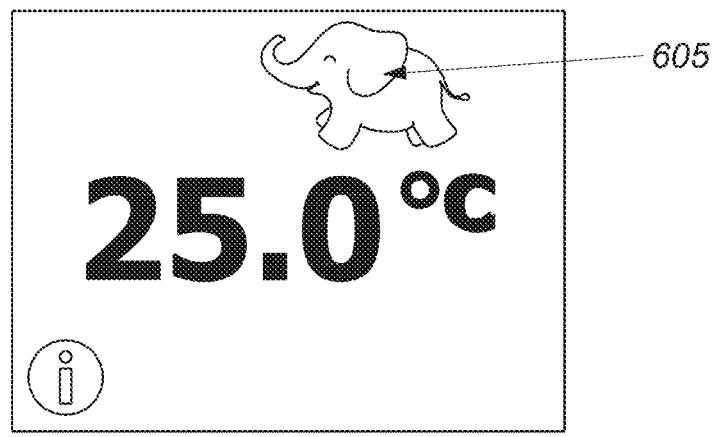
FIG. 6A is a screenshot of a neonatal operating mode with a softening element.
Figure 6B:
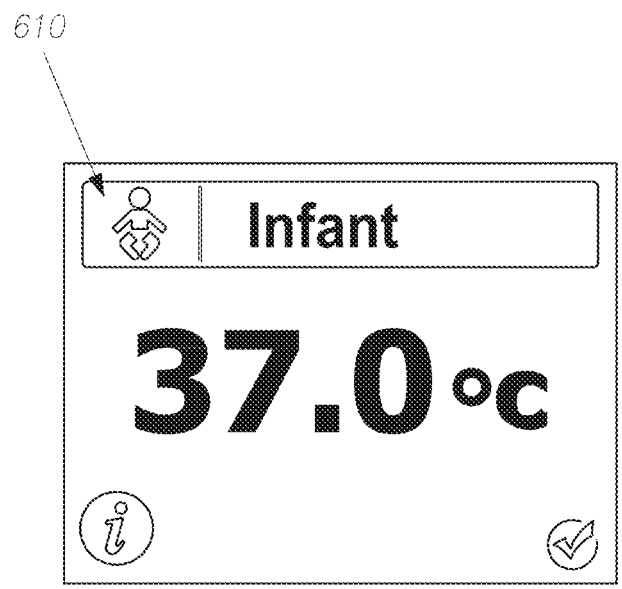
FIG. 6B is a screenshot of another example neonatal operating mode.

FIG. 6A illustrates a screenshot of an example neonatal operating mode with a softening element 605. The softening element can be, for example, child friendly graphics or features associated with the patient or the patient's family. The graphics or features can be animated or static. In an embodiment, the softening element is an animation of a dancing elephant. In an embodiment, the user interface of the neonatal circuit is simpler than the corresponding adult screen. In an embodiment, the neonatal display will not offer options to change the temperature set point as the neonatal mode will operate on one temperature or dewpoint setting. This simplifies the interface to the user by only offering options that are relevant to the operating mode or corresponding circuit connected. FIG. 6B illustrates a screenshot of another neonatal operating mode. The neonatal indicator 610 can be used to indicate with an image, words, colors, icons, or any combination of these or the like to indicate that the apparatus is in the neonatal operating mode.

Figure 7A:
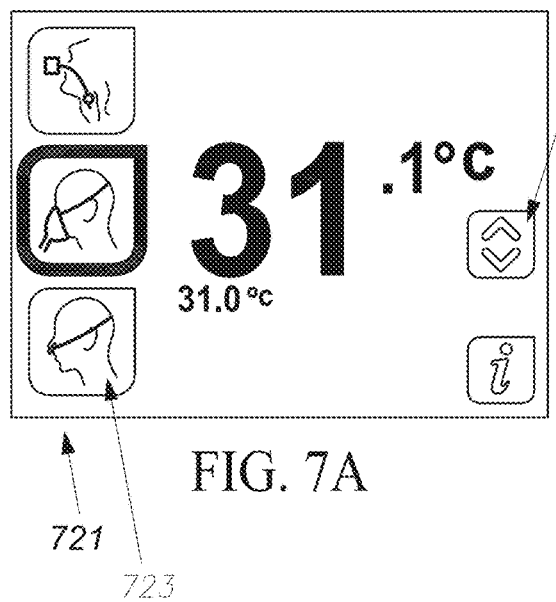
FIG. 7A is a screenshot of a non-invasive operating mode with a button to access a temperature or dewpoint set point adjustment panel in a first embodiment.
Figure 7B:
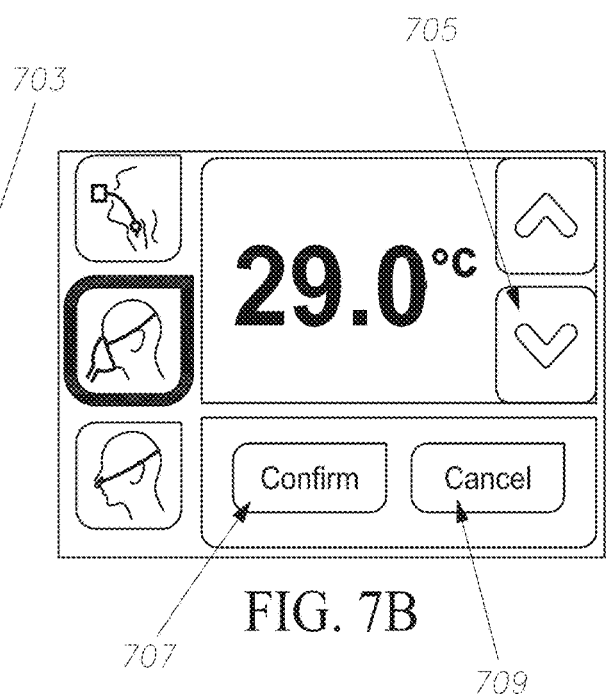
FIG. 7B is a screenshot of a temperature or dewpoint set point adjustment panel in a first embodiment.

FIG. 7A illustrates an embodiment of a display screen similar to the display screen of FIG. 1B. In this embodiment, a. button 703 that allows for a temperature adjustment is provided. On touching the button, a temperature adjustment panel will be displayed where the user can select to change the set point of the temperature. An embodiment of the panel is shown in FIG. 7B. In an, embodiment, the temperature adjustment is limited to a certain predefined set of values that are specific to a particular type of respiratory support. For example, in one embodiment, only one of three values can be chosen. For example, these three values can be 31° C., 29° C., and 27° C. In an embodiment, the default temperature is 29° C. In an embodiment, the default temperature value can be customized by the user in the advanced settings menu. In an embodiment, the breathing assistance apparatus 20 can remember the user-selected change of the set point of the temperature during shutdown and return to that setting after start-up. The temperature adjustment button 703 is allowed in certain operating modes where adjustment is permitted. For example, in an embodiment illustrated in FIG. 1A, in the invasive operating mode, temperature adjustment is not permitted, and thus not displayed. In other embodiments, temperature adjustment is permitted in some other subset of operating modes or in all operating modes. The panel of FIG. 7B includes temperature control buttons 705, a confirm button 707, and a cancel button 709. These buttons assist a user to select an, appropriate temperature setting. The temperature control buttons 705 will be greyed out if it is not possible to elevate or lower the set point further. In an embodiment, the temperature control buttons 703 can be entirely disabled through the use of advanced settings to prevent undesirable changes. In an embodiment, the default temperature values can be set through the use of advanced settings.

In some embodiments, a set point selected by a user for an operating mode can be retained when switching between operating modes. In certain implementations, the user can indicate that the customized set point should be retained when switching between operating modes, for example by indicating the selected set point should be persistent. For example, if the user changes a temperature set point of a first operating mode (e.g., a non-invasive operating mode) from a default value to a customized temperature set point of 28° C., then switches operation to a second operating mode (e.g., an invasive operating mode) that uses a temperature set point of 31° C., when the user switches back to the first operating mode the customized temperature set point of 28° C. will be used instead of the default value. The customized set point can be retained until the user selects a different set point, which may also be persistent. In some embodiments, the user can indicate that the customized set point be used for a limited number of operating modes. The user can indicate that the customized set point should be temporary, reverting to the default value after an indicated number of uses or an indicated or default length of time. For example, the customized set point can be configured to change back to the default value after the machine is powered down, after a single use, after 8 hours of use, or the like.

Figure 7C:
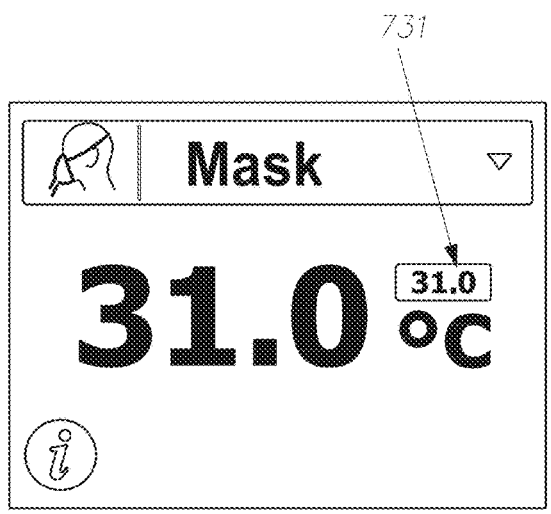
FIG. 7C is a screenshot of a non-invasive operating mode with a button to access a temperature or dewpoint set point adjustment panel in a second embodiment.
Figure 7D:
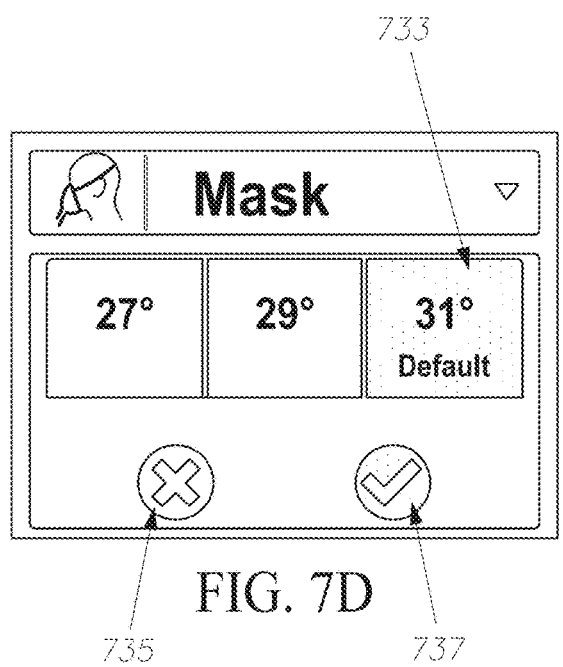
FIG. 7D is a screenshot of a temperature or dewpoint set point adjustment panel in a second embodiment.

FIGS. 7C-7D are screenshots that illustrate alternative embodiments to the embodiments of FIGS. 7A and 7B. FIG. 7C illustrates an embodiment in which a selected temperature set point 731 also doubles as the set point adjustment button. When selected, the temperature set point button 731 will bring up the temperature set point selection panel, such as that shown in FIG. 7D. FIG. 7D illustrates an embodiment where all of the allowed set points are displayed at the same time as option buttons and the selected set point is highlighted in a different color to show it is the selected set point. The default set point is emphasized by a text label 733 showing 'default' underneath. The user can click on a cross button 735 or a tick button 737 to cancel or confirm the selected set point change.

Since the interface to the breathing assistance apparatus 20 is a touch screen and the breathing assistance apparatus 20 will typically be at knee height and below the eye line, it is possible to accidentally touch and change the current operating status of the breathing assistance apparatus 20 and thus deliver inappropriate respiratory support to the patient. To ensure the action of changing an operating mode or set point is deliberate action, a two-step process may be enforced for changing the operating mode, and a three step process may be enforced for changing the set point where allowed, for example, in a non-invasive operating mode. This also ensures that all the information necessary for making the change is available to the user only at the time it is required, keeping the interface uncluttered at all other times.

FIGS. 8A-8D are screenshots that illustrate an embodiment of an information screen showing settings that can be hidden. These hidden settings are extended features that support different operating modes and maximize the ease to configure the breathing assistance apparatus 20. For example, the hidden settings can be used for set point adjustment, language selection, etc. A graphical passcode is implemented to restrict access to these hidden settings.

In some embodiments, a language can be selected using, for example, the hidden settings described herein. The language can be chosen from a number of pre-loaded languages provided by default. The languages provided may be updated through a number of means, such as through connection of a storage device (e.g., a USB drive, thumb-drive, memory card, cartridge, or the like). When a language is selected, menu options, instructions, information, alerts, alarms, and the like can be presented in that language. In an embodiment, the language can be selected during startup. In other embodiments, a default language can be selected at manufacture based on the intended recipient of the breathing assistance apparatus 20, and the language can be changed through the use of menu selections.

Figure 8A:
FIG. 8A is a screenshot of an invasive operating mode with a button to access an information screen.
Figure 8B:
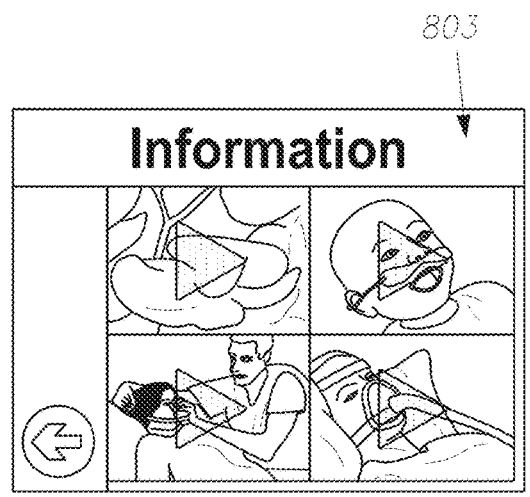
FIG. 8B is a screenshot of an information screen with a title banner that also provides access to a passcode panel.
Figure 8C:
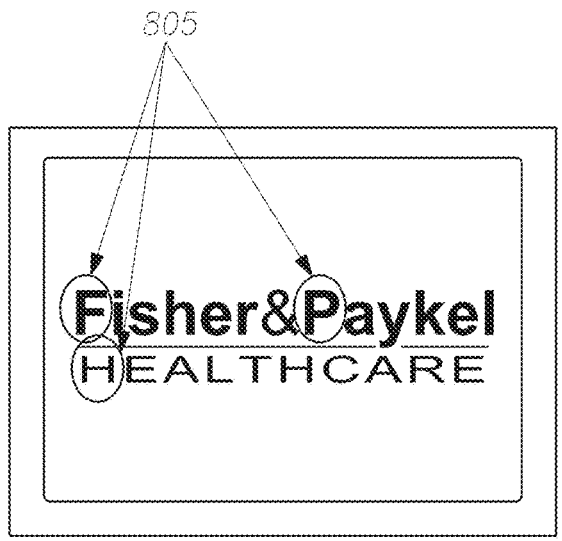
FIG. 8C is a screenshot of a passcode panel with hidden buttons to access hidden settings on the information screen.
Figure 8D:
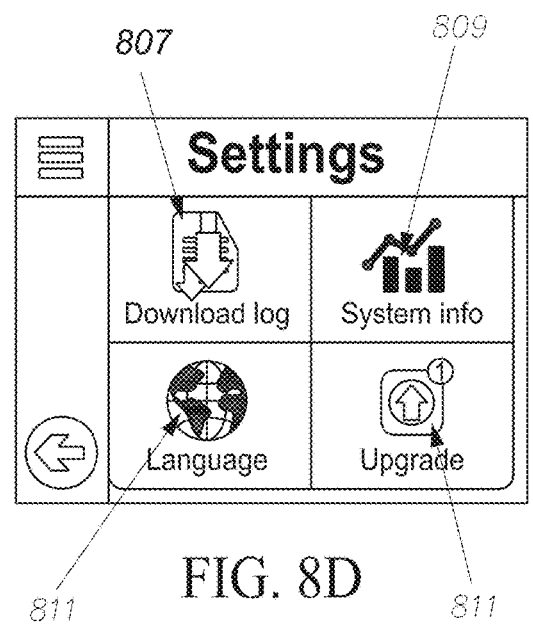
FIG. 8D is a screenshot of an information screen with hidden settings made accessible.

In an embodiment, the hidden settings are accessed, for example, by initially selecting an information button 801. The information button 801 brings up au information screen, such as illustrated in FIG. 8B. The information screen includes only limited information and settings relevant to a primary user. In order to access the hidden settings, the user should click on an information bar 803. In an embodiment, a user should provide an extended touch to the information bar 803. In another embodiment, access may be provided by carrying out similar actions on another screen (e.g., an alarm screen). This will bring up a passcode panel, that displays a graphic, such as the Fisher & Paykel Healthcare logo, for example, as illustrated in FIG. 8C. In other embodiments, alternative displays or graphics can be provided, and the present disclosure is not limited to a passcode panel comprising a manufacturer's logo. Such a graphics or logo page allows for the entry of a passcode without the need for a bulky or significantly sized keyboard or number pad. It also provides for a graphical and easy to remember passcode entry system. In order to access the hidden settings, a passcode must be entered on the passcode panel. For example, in FIG. 8C, the passcode is entered by pushing the 'F', 'P', and 'H' buttons 805. If the user fails to enter the correct passcode, they are given the option to retry or cancel their attempt to access the hidden settings. Once the passcode is entered correctly, the information screen will be displayed once more. However it will now show the settings that were hidden prior to correctly entering the passcode. These hidden settings are illustrated in FIG. 8D. FIG. 8D includes advanced features, such as a download log feature 807, a language selection feature 811, a software upgrade feature 813, and a diagnostic feature 809. This passcode touch sequence is not a typical action that the typical user would be expected to carry out and hence it reduces the risk of the typical user navigating to advanced settings. In alternative embodiments, multi-touch gestures or a confirmation screen can be used instead of hidden settings.

In an embodiment, the software of the breathing assistance apparatus 20 can be upgraded. For example, this can be done by connecting a USB device, or through wired or wireless communications. On plugging a USB key into the breathing assistance apparatus 20, the controller will be notified of the USB event. In an embodiment, the controller will automatically scan the USB key files and determine if there is an upgrade file stored within the USB key. If the file is found, a message box will be displayed on the user interface asking the user if they would like to upgrade the software. The user can press the 'yes' button to start the upgrade process or the 'no' button to carry on with normal operation. If the yes button is chosen, the display will switch to the upgrade screen. In another embodiment, the controller will automatically scan the USB key files and determine if there is an upgrade file stored within the USB key. If an upgrade file is found on the USB key, an upgrade selection 811 (which is otherwise grayed out) will become an available option for the user to click to start the upgrade process. In some embodiments, when the user holds down the power button while the breathing assistance apparatus 20 is powering up, if a USB key is plugged in, the controller will start the upgrade process. The user will be advised not to unplug or reset the breathing assistance apparatus 20 while the upgrade is in progress. A progress bar will be displayed to show the upgrade progress. After completing the upgrade, the upgrade screen can advise the user to unplug the USB key and restart the breathing assistance apparatus 20. In an embodiment, upgrades are only allowed while the breathing assistance apparatus 20 is not in use. In an embodiment, upgrades will be accepted at any time during use.

Figure 8E:
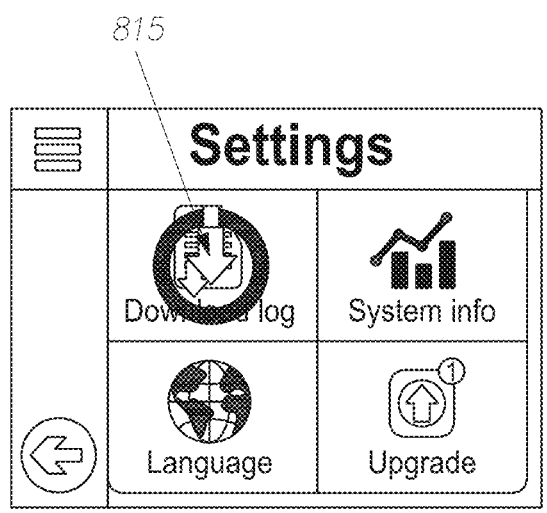
FIG. 8E is a screenshot of an information screen indicating that a log is being downloaded.

FIG. 8E is a screenshot that illustrates an embodiment of an information screen indicating that a log is being downloaded with a download progress indicator 815. If the download log feature 807 is selected by a user, the apparatus can transmit log information to a storage medium (e.g., a USB stick or other memory device) and/or through wired or wireless communication to another device (e.g., through a wireless internet connection, Bluetooth connection, etc.). The download progress indicator 815 can be animated to indicate that the download is in progress. In some embodiments, the download progress indicator 815 can change (e.g., through an animation, progress bar or icon, or any sequence of images) to represent a percentage or fraction of the log that has been downloaded.

Figure 9:
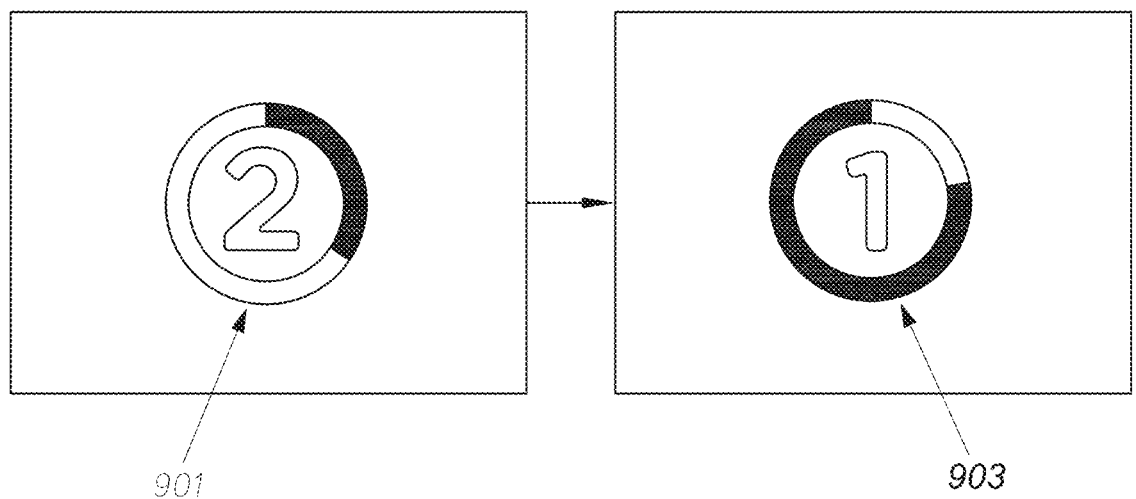
FIG. 9 is a series of screenshots showing a countdown mode.

FIG. 9 is a screenshot that illustrates an embodiment of an assisted intentional shutdown sequence. As the breathing assistance apparatus 20 is typically mounted at knee height and below eye level, it may be possible to unintentionally turn off the breathing assistance apparatus 20 by accidentally pressing the power button and thus cease delivering respiratory support to the patient. To ensure shutdown is a deliberate action, it is necessary to hold the power button down, for 2 seconds. Count down visuals 901, 903 are provided to the user to assist the user to carry out this action. The power button can be a hardware button or software button, depending on the type of the breathing assistance apparatus 20.

Figure 10A:
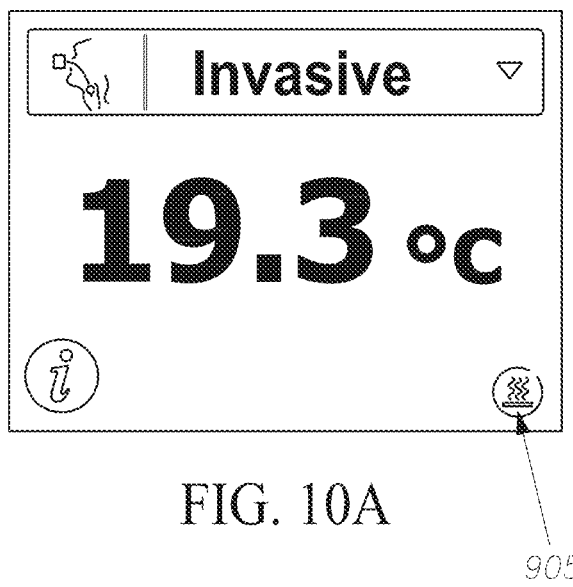
FIGS. 10A and 10B are a series of screenshots showing a status indicator.
Figure 10B:
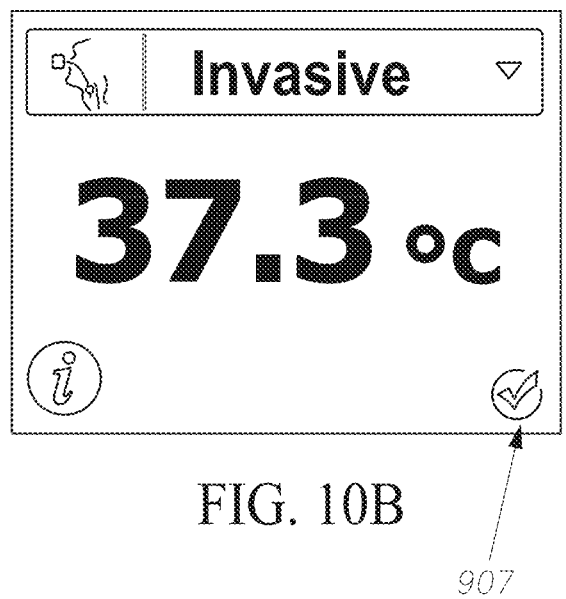

FIGS. 10A-10B are screenshots that illustrate an embodiment of a display screen comprising status indicators 905, 907 of the breathing assistance apparatus 20. Since the breathing assistance apparatus 20 supports multiple operating modes that use different default set points, the status indicators 905, 907 can help the user to understand the status of the breathing assistance apparatus 20 without memorizing set points for all operating modes. It is also observed that under some circumstances, the breathing assistance apparatus 20 takes some time to react to changes in set up, so fluctuations may occur in the dewpoint displayed. The status indicators 905, 907 can assist the user in understanding and dealing with these fluctuations. FIG. 10A illustrates an embodiment in which the status indicator 905 is showing an animated heating symbol (which can repeat or be substantially continuous) to indicate the breathing assistance apparatus 20 is warming up. FIG. 10B illustrates an embodiment in which the status indicator 907 is showing a tick mark to indicate the breathing assistance apparatus 20 is ready to be used. In some embodiments, the status indicators 905, 907 can also be used to indicate other types of status changes.

The breathing assistance apparatus 20 can be configured to provide a plurality of different operating modes that utilize different set points and/or configurations. To facilitate determining the operating status of the breathing assistance apparatus and to reduce challenges associated with remembering set points for different operating modes, the display 40 can present information to the user using one or more status indicators and other associated information, on a single screen that can convey in a relatively simple manner the working status of the breathing assistance apparatus 20 and/or a suggested user action (e.g., connecting the breathing assistance apparatus 20 to the patient).

Figure 11A:
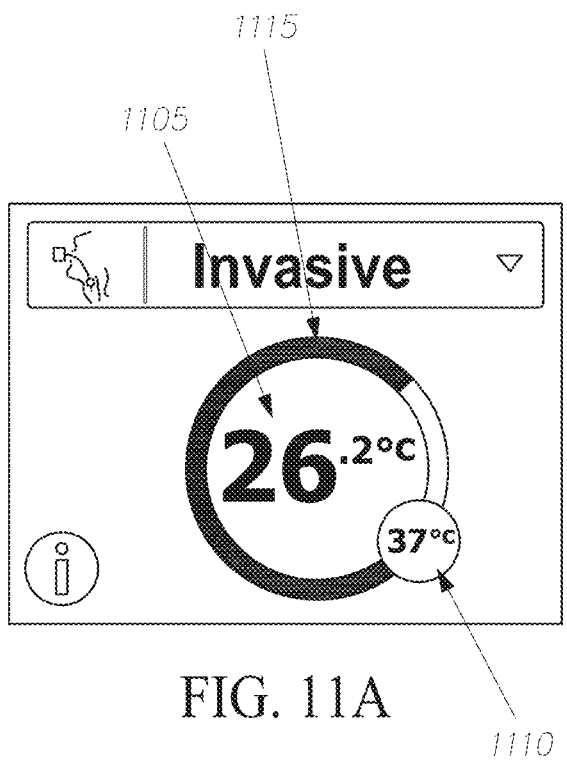
FIGS. 11A and 11B are screenshots of a display showing a current temperature or status, a temperature or dewpoint set point, and a progress bar.
Figure 11B:
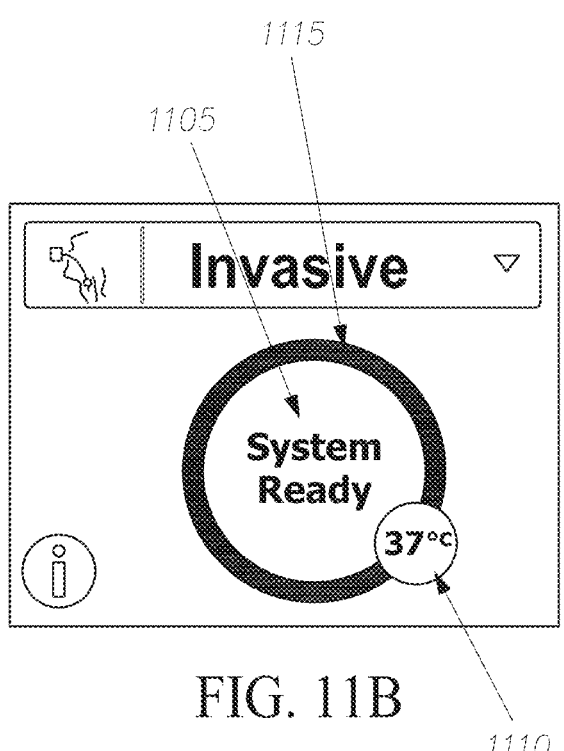

FIGS. 11A and 11B are screenshots that illustrate an embodiment of a display screen comprising a current temperature or status 1105, a temperature or dewpoint set point 1110, and a progress bar 1115. The set point 1110 can be configured to be displayed on the user interface along with the measured or calculated temperature 1105 and an orbital progress bar 1115 to illustrate the change of temperature, as illustrated in FIG. 11A. In addition, when the temperature reaches the set point or when the apparatus is performing a particular task (e.g., warming up), the display can show in the status area 1105 text, icons, graphics, or the like indicating the system status, as illustrated in FIG. 11B.

Figure 12A:
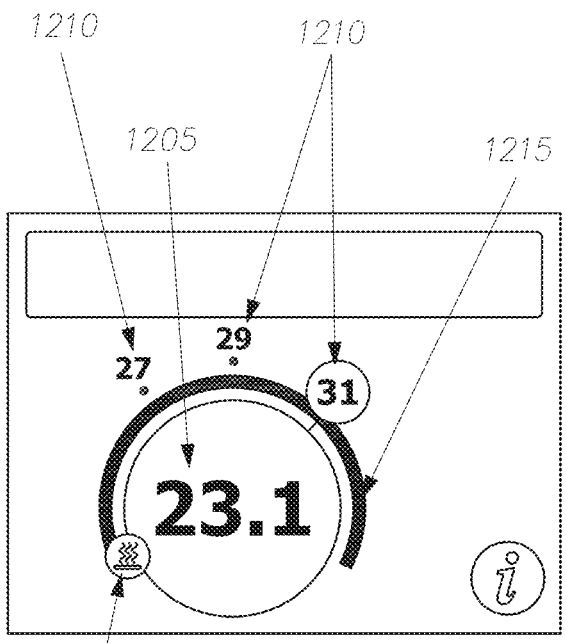
FIGS. 12A-12C are screenshots of a display showing a current temperature, a temperature or dewpoint set point, an orbital progress indicator, and status indicators.
Figure 12B:
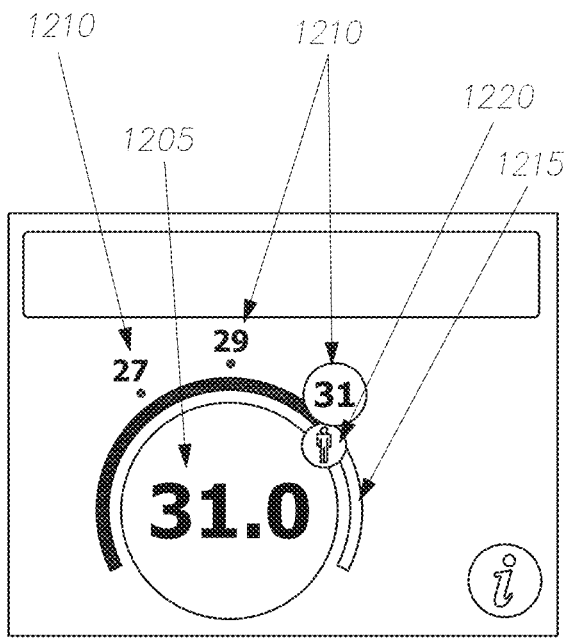
Figure 12C:
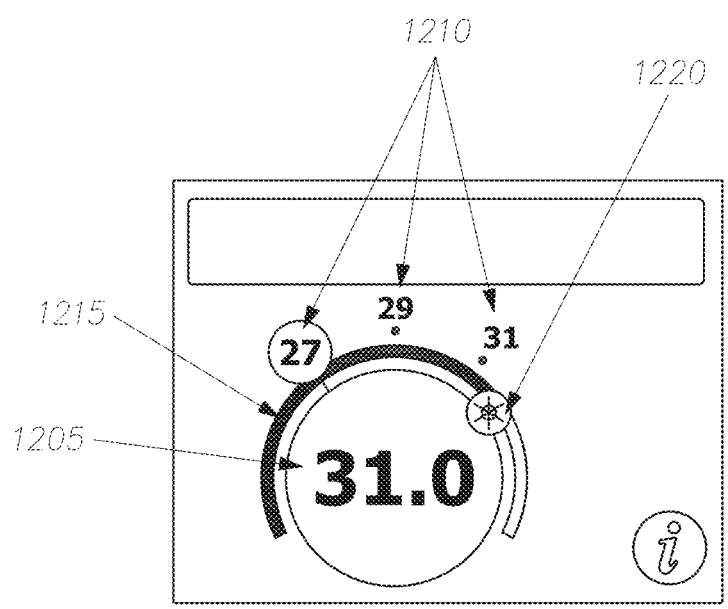

FIGS. 12A-12C are screenshots that illustrate an embodiment of a display screen comprising a current temperature 1205, a temperature or dewpoint set point 1210, an orbital progress indicator 1215, and status indicators 1220. The status indicator 1220 can be coupled with the set point adjustment selections 1210, and the selected set point can be differentiated from unselected set points graphically. For example, available set points 1210 can be indicated on the orbital progress indicator 1215. The selected set point can be highlighted using colours and shapes. Status indicators 1220 can be used to indicate, for example and without limitation, heating, cooling, ready, and connecting to a patient. The status indicators 1220 can be used to notify the user about the system status. In some embodiments, the status indicator 1220 can move along the orbital path of the progress indicator 1215 as the temperature changes to indicate progress. The status indicator 1220 can change automatically to update the user about the system status. The color of the orbit progress indicator 1215 can change with the system status, such as when the device is warming up the orbit can be blue in color and when the device is ready to use the orbit can be green in color.

Figure 13:
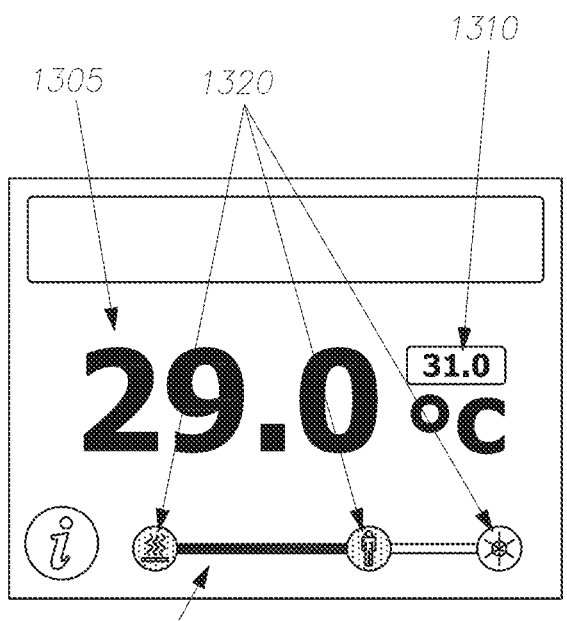
FIG. 13 is a screenshot of a display showing a current temperature, a temperature or dewpoint set point, a horizontal progress bar, and status indicators.

FIG. 13 is a screenshot that illustrates an embodiment of a display screen comprising a current temperature 1305, a temperature or dewpoint set point 1310, a horizontal progress bar 1315, and status indicators 1320. The status indicators 1320 can be overlaid on the progress bar 1315 to indicate system status as a function of temperature. For example, if the temperature exceeds the set point, which can be indicated using an icon of a person, a cooling icon can be shown to show that the gases are cooling. As another example, while the gases are being heated the system heating icon can be highlighted on the progress bar 1315. The color of the progress bar 1315 can change with system status, as described herein.

Figure 14:
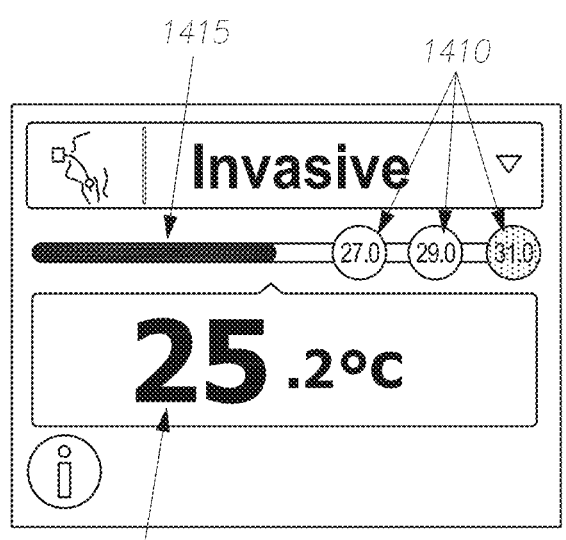
FIG. 14 is a screenshot of a display showing a current temperature, a temperature or dewpoint set point, and a horizontal progress bar.

FIG. 14 is a screenshot that illustrates an embodiment of a display screen comprising a current temperature 1405, temperature or dewpoint set points 1410, and a horizontal progress bar 1415. The selected set point can be graphically distinguished from other available set points. The progress bar 1415 can be used to indicate the current temperature relative to the selected set point. As described herein, the progress bar can change color based at least in part on system status, current temperature, and/or temperature or dewpoint set points.

Figure 15A:
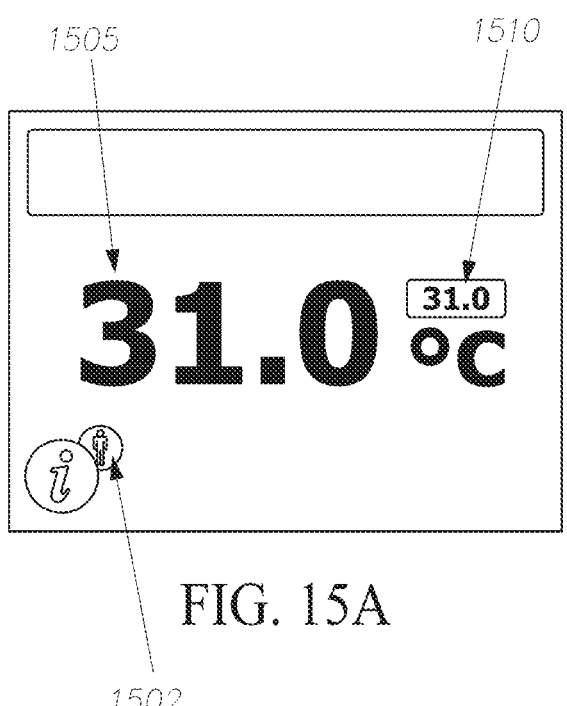
FIGS. 15A and 15B are screenshots of a display showing a current temperature, a temperature or dewpoint set point, status indicators, and a legend indicating the meaning of the status indicators.
Figure 15B:
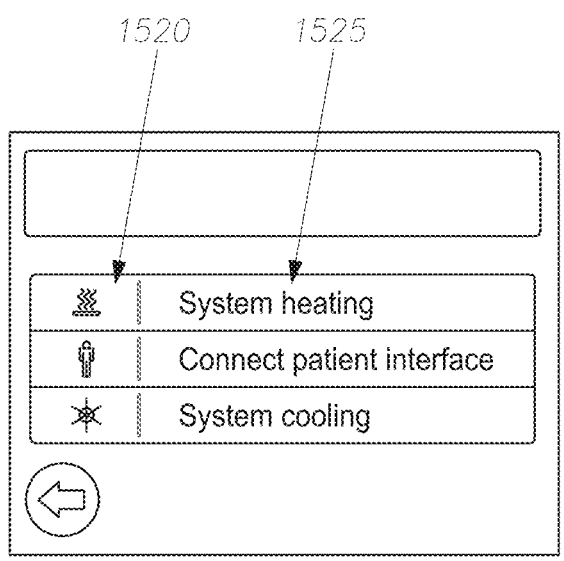

FIGS. 15A and 15B are screenshots that illustrate an embodiment of a display screen comprising a current temperature 1505, a temperature or dewpoint set, point 1510, status indicators 1520, and a legend 1525 indicating the meaning of the status indicators 1520. This embodiment can be used to reduce a size or appearance of the status indicators 1520. For example, the status indicator 1520 can be a graphical icon that automatically updates itself and that is coupled with the information button. When the icon is clicked or selected, the display 40 can show the legend 1525 with definitions of the icons in text to assist the user in understanding the status indicator 1520.

The colors of various elements in the displayed screens of FIGS. 11-15 can change to indicate system status, current temperature, a difference between the set point and temperature, and the like. The color and changes in color can help a user to determine the operating state of the breathing assistance apparatus. For example, the current temperature indicator, the set point indicator, progress bars, status indicators, and the like can change color or undergo similar graphical changes to correspond to operating conditions of the breathing assistance apparatus.

Although the disclosure herein has been presented in terms of some embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice embodiments encompassed by this disclosure. Accordingly, the scope of this disclosure is intended to be defined only by the claims that follow.

What is claimed is:

1. A breathing assistance apparatus comprising:
   a humidifier configured to provide respiratory support to a patient; and
   a display forming part of the humidifier, the display adapted to provide visual information to a user,
   wherein the display changes from a current screen, when an alarm related to a component of the breathing assistance apparatus is activated, to a dedicated-alarm screen configured to focus a user's attention on the alarm,
   wherein in response to multiple alarms being activated, only one of the multiple alarms is presented to the user at a single time in the dedicated alarm screen, wherein the only one of the multiple alarms presented to the user is an activated alarm with a highest severity level, and
   wherein the display is configured to cycle an animation of the alarm related to the component of the breathing assistance apparatus until an issue relating to the alarm is resolved, the animation comprising displaying the breathing assistance apparatus, zooming towards an affected area of the breathing assistance apparatus in an image of the breathing assistance apparatus, and highlighting in a visually distinctive color at least a portion of the affected area of the breathing assistance apparatus in the image of the breathing assistance apparatus on the display and animating a corrective action to be performed using graphical elements as part of the animation.

2. The breathing assistance apparatus of claim 1, further comprising a speaker configured to be activated when the alarm is activated.

3. The breathing assistance apparatus of claim 2, further comprising an alarm mute button display on the display when the alarm is activated, wherein, in response to being activated by the user, the alarm mute button display is configured to silence the speaker for a predetermined period of time.

4. The breathing assistance apparatus of claim 3, wherein the alarm mute button display on the display, in response to being activated by the user whilst the speaker is silenced, is configured to activate the speaker.

5. The breathing assistance apparatus of claim 1, wherein the display is configured to illustrate information needed to remedy the alarm when the alarm is activated.

6. The breathing assistance apparatus of claim 5, wherein the animation further comprises the information needed to remedy the alarm.

7. The breathing assistance apparatus of claim 1, wherein in response to the multiple alarms being addressed, the display is configured to return to the current screen.

8. The breathing assistance apparatus of claim 1, wherein the display is dedicated to present the alarm to the user when the alarm is activated so as to draw the user's focus to the issue causing the alarm.

9. The breathing assistance apparatus of claim 1, wherein in response to multiple alarms being activated, the severity levels of the multiple alarms are based on a predetermined modal importance, an order in which the multiple alarms occur, or a combination thereof.

10. The breathing assistance apparatus of claim 1, wherein the display is configured to display an indicator prior to changing from the current screen.

11. The breathing assistance apparatus of claim 2, wherein selecting or activating the indicator is configured to bring up a warning screen configured to display information on how to resolve a warning condition.

12. The breathing assistance apparatus of claim 1, wherein highlighting the affected area in the visually distinctive color further comprises the affected area flashing in the visually distinctive color.

13. A breathing assistance apparatus that provides respiratory support to a patient, the breathing assistance apparatus comprising:
- a humidifier configured to provide respiratory support to a patient; and
- a display forming part of the humidifier, the display adapted to provide visual information to a user,
- wherein the visual information comprises one or more alarms, and
- wherein a level of detail in the one or more alarms provided to the user is configured to be selectable by the user of the breathing assistance apparatus, and
- wherein in response to multiple alarms being activated, only one of the multiple alarms is presented to the user at a single time in a dedicated alarm screen configured to focus a user's attention to the alarm, wherein the only one of the multiple alarms presented to the user is an activated alarm related to a component of the breathing assistance apparatus with a highest severity level, and
- wherein the display is configured to cycle an animation of the alarm related to the component of the breathing assistance apparatus until an issue relating to the alarm is resolved, the animation comprising displaying the breathing assistance apparatus, zooming towards an affected area of the breathing assistance apparatus in the image of the breathing assistance apparatus, and highlighting in a visually distinctive color at least a portion of the affected area of the breathing assistance apparatus in the image of the breathing assistance apparatus on the display and animating a corrective action to be performed using graphical elements as part of the animation.

14. The breathing assistance apparatus of claim 13, wherein the level of detail comprises one or more steps to address conditions causing the alarm, or potential causes for the alarm as determined by the breathing assistance apparatus.

15. The breathing assistance apparatus of claim 13, wherein after a first level of detail is displayed, the level of detail is configured to change after a passage of time or a user input or action.

16. The breathing assistance apparatus of claim 13, wherein the level of detail comprises one or more operations to be performed using settings of the breathing assistance apparatus, operations requiring the user to access hardware components of the breathing assistance apparatus, or operations requiring disassembly of portions of the breathing assistance apparatus.

17. The breathing assistance apparatus of claim 13, wherein highlighting the affected area in the visually distinctive color further comprises the affected area flashing in the visually distinctive color.

* * * * *

UNITED STATES PATENT AND TRADEMARK OFFICE
CERTIFICATE OF CORRECTION

| | |
|---|---|
| PATENT NO. | : 12,397,124 B2 |
| APPLICATION NO. | : 15/029189 |
| DATED | : August 26, 2025 |
| INVENTOR(S) | : Warushahennedige Hansinie Soysa et al. |

It is certified that error appears in the above-identified patent and that said Letters Patent is hereby corrected as shown below:

In the Specification

Column 2, Line 34, delete "set point, adjustment" and insert -- set point adjustment --.

Column 4, Line 24, delete "requires attention" and insert -- requires attention. --.

Column 7, Line 5, delete "20 and, the" and insert -- 20 and the --.

Column 7, Line 20, delete "device. In, some" and insert -- device. In some --.

Column 8, Line 29, delete "operate in, an" and insert -- operate in an --.

Column 9, Line 14-15, delete "remaining operating. modes" and insert -- remaining operating modes --.

Column 10, Line 2, delete "the Like. Parameters" and insert -- the like. Parameters --.

Column 11, Line 32, delete "alarm will, also" and insert -- alarm will also --.

Column 13, Line 67, delete "control (e g, manual" and insert -- control (e.g., manual --.

Column 14, Line 43, delete "information screen, will" and insert -- information screen will --.

Column 15, Line 5, delete "embodiment, a. button" and insert -- embodiment, a button --.

Column 15, Line 9, delete "In an, embodiment," and insert -- In an embodiment, --.

Signed and Sealed this
Ninth Day of December, 2025

John A. Squires
*Director of the United States Patent and Trademark Office*

CERTIFICATE OF CORRECTION (continued)
U.S. Pat. No. 12,397,124 B2

Column 15, Line 29, delete "select an, appropriate" and insert -- select an appropriate --.

Column 16, Line 47, delete "up au information" and insert -- up an information --.

Column 16, Line 55, delete "passcode panel, that" and insert -- passcode panel that --.

Column 18, Line 1, delete "button down, for" and insert -- button down for --.

Column 18, Line 34, delete "associated information, on" and insert -- associated information on --.

Column 19, Line 31, delete "dewpoint set, point" and insert -- dewpoint set point --.

In the Claims

Column 20, Claim 11, Line 60, delete "claim 2, wherein" and insert -- claim 10, wherein --.